United States Patent [19]

Richter et al.

[11] 3,943,154

[45] Mar. 9, 1976

[54] ACYLAMIDES OF BETA-CYANO-ETHENESULFONYL SUBSTITUTED AMINOARENES

[75] Inventors: Sven U. K. A. Richter, Boston, Mass.; Alexandros K. Tsolis; Elefteria A. Tsolis, both of Athens, Greece

[73] Assignee: Sanitized Incorporated, New York, N.Y.

[22] Filed: Mar. 2, 1973

[21] Appl. No.: 337,637

[52] U.S. Cl. .................. 260/397.6; 71/87; 71/88; 71/90; 71/100; 71/103; 424/200; 424/210; 424/211; 424/228; 424/229; 424/244; 424/248; 424/270; 424/301; 424/304; 424/309; 424/321; 424/324; 424/330; 260/239 EP; 260/239.6; 260/239.9 S; 260/239.7; 260/247.1 B; 260/306.8 D; 260/465 D; 260/465 E; 36/470; 260/551 P; 260/556 A; 260/556 AR; 260/558 S

[51] Int. Cl.² .................................. C07C 121/70

[58] Field of Search ........ 260/397.6, 465 E, 465 K, 260/465 D

[56] References Cited
UNITED STATES PATENTS

| | | | |
|---|---|---|---|
| 3,159,532 | 12/1964 | Heininger et al. | 260/465 K |
| 3,541,119 | 11/1970 | Richter et al. | 260/397.6 |

*Primary Examiner*—Sherman D. Winters
*Attorney, Agent, or Firm*—Hubbell, Cohen & Stiefel

[57] ABSTRACT

Acylamides of $\beta$-X-ethenesulfonyl substituted aminoarenes in which the acyl moiety is an organic sulfonic, sulfinic or sulfenic acid group; an organic phosphoric, thiophosphoric, phosphonic, thiophosphonic, or phosphinic acid group; or the sulfinyl group (O=S=). Compounds within the designated class of materials are bioactive, i.e., they control the growth and activity of varying types of plant and animal organisms, e.g., microorganisms or the like.

3 Claims, No Drawings

ACYLAMIDES OF BETA-CYANO-ETHENESULFONYL SUBSTITUTED AMINOARENES

BACKGROUND OF THE INVENTION

This invention relates to novel acylamides of β-X-ethenesulfonyl substituted aminoarenes, and to methods for controlling the growth of plant and animal organisms utilizing such materials.

As used herein, the references to the bioactive characteristics of the compounds of the present invention pertain to their use for killing or inhibiting the growth or functions of plant or animal organisms, e.g., microorganisms such as bacteria, fungi, protozoa or the like, or nematodes, snails, or other higher plant or animal systems.

Various ethenesulfonyl arenes have heretofore been proposed as useful bioactive compounds. Such materials include, for example, the amino and acylamidoarenesulfonyl-substituted acrylonitriles, acrylamides, acrylates and the like disclosed in copending Richter application Ser. No. 228,410 filed Feb. 22, 1972, now U.S. Pat. No. 3,821,399, owned by the assignee of the present invention. Methods for the preparation of compounds of the preceding types are disclosed, for example, in Richter and Tsolis U.S. Pat. No. 3,541,119 granted Nov. 17, 1970, also owned by the assignee of the present invention.

Beta-substituted ethene-aminoarenes of the above types find application as bactericides, fungicides, herbicides or the like. One material so useful is 3-(4-aminobenzenesulfonyl) acrylonitrile [or (2-cyanoethene)sulfonyl-4-aminobenzene]; this compound may be conveniently and economically prepared employing the technique described in the aforesaid Richter and Tsolis patent. While this material is a powerful bioactive substance, its use is undesirable for certain applications, the amino group reacting with many substances and the compound itself having a strong yellow color. Moreover, this and similar aminoarenes tend to be irritant to warm-blooded animals. As disclosed in the aforesaid application, various of the carboxylamido derivatives of the β-X-ethenesulfonyl substituted aminoarenes are less reactive, less irritant, and generally have less intense colors than the corresponding aminoarenes themselves. These carboxamido compounds possess bioactivities equal to and, frequently, greater than those of the corresponding base aminoarenes.

It has now been discovered that other N-acylamido derivatives of β-X-ethenesulfonyl-substituted aminoarenes, viz., various sulfonamido, sulfinamido, sulfenamido, phosphoramido, thiophosphoramido, phosphinamido, phosphonamido, and thiophosphonamido, derivatives thereof, may be utilized in the same manner as the carboxamido compounds as bioactive materials for controlling the growth of plant and animal organisms, while frequently also providing increased biological activity, lesser reactivity, better color and additional useful properties.

SUMMARY OF THE INVENTION

In accordance with the present invention acylamides of β-X-ethenesulfonyl-substituted aminoarenes are provided, having one of the following formulas:

A. $R'[S(O)_pNH—ArSO_2CH=CHX]_m$,
B. $O=S=NArSO_2CH=CHX$, and
C. $(R'')_n—Z+NH—Ar—SO_2CH=CHX]_q$ In the sulfonamido, sulfinamido, sulfenamido and sulfinylamido compounds of Formulas (A) and (B) above:

R' is an aliphatic, cycloaliphatic or araliphatic group having up to 16 carbon atoms, e.g., an alkane having up to 16 carbon atoms and in which the hydrogens may be replaced with halogen from monosubstitution to persubstitution, or in which the omega hydrogen may be replaced by phenyl or nitro; an alkene having from 2 to 16 carbon atoms in the alkene moiety thereto and in which one hydrogen may be substituted by nitro, cyano or phenyl, the phenyl moiety being unsubstituted or having up to 5 ring hydrogens substituted by alkyl of from 1 to 6 carbon atoms or halogen, or up to 3 ring hydrogens substituted by nitro; an arene having up to 10 carbon atoms, e.g., benzene or naphthalene or a substituted arene having up to 10 carbon atoms and in which the ring hydrogens may be replaced with up to 4 substituents from among alkyl, haloalkyl or alkenyl having up to 16 carbon atoms, halogen, nitro (up to 3 groups), hydroxy, alkoxy having up to 16 carbon atoms, amino, carboxyl, carbalkoxy having up to 16 carbon atoms in the alkoxy moiety thereof, cyano, the carboxamido group —CONH—Ar—SO$_2$CH=CH—X wherein X and Ar are as defined below, dihalocyclopropenyl, or fluorosulfonyl; or an acylamidothiadiazole group;

Ar is an arene having up to 10 carbon atoms, e.g., benzene or naphthalene, or a substituted arene having up to 10 carbon atoms and in which up to 8 of the ring hydrogens may be replaced by alkyl having from 1 to 6 carbon atoms or halogen, or in which up to 3 of the ring hydrogens may be replaced by nitro groups;

X is an electron-attracting or electron-withdrawing group, preferably —CN; —CONH$_2$; COOR$_1$; COSR$_1$; —NO$_2$; —SOR$_2$; —SO$_2$R$_2$; —F; or —CF$_3$; and in which:

R$_1$ is an aliphatic or cycloaliphatic group having from 1 to 12 carbon atoms wherein the hydrogen atoms may be replaced by halogen from monosubstitution to persubstitution, e.g., alkyl, cycloalkyl, alkenyl, alkynyl or a halogen-substituted alkyl, cycloalkyl, alkenyl, or alkynyl, and including halogen-substituted alkenyl groups in which one or both of the ethylenic hydrogens may be substituted by halogen and a hydrogen on the omega carbon may be substituted by phenyl; a phenyl group or a phenyl alkyl having up to 16 carbon atoms in the alkyl moiety thereof, in which the phenyl moieties thereof may be substituted by alkyl of up to 6 carbon atoms, halogen, nitro, amino or carboxamido having up to 12 carbon atoms; 2-phenylvinyl; a dialkyl-tin or trialkyl-tin, the alkyl moiety of which has from 2 to 12 carbon atoms; or a triphenyl-tin;

R$_2$ is an arene having up to 10 carbon atoms, e.g., benzene or naphthalene, or a substituted arene having up to 10 carbon atoms and substituted by halogen or nitro;

p is 0, 1 or 2; and m is an integer of from 1 to 3.

The compounds of Formula (C) above are β-X-ethenesulfonyl-substituted phosphor-, thiophosphor-, phosphin-, phosphon-, or thiophosphonamidoarenes wherein:

R'' is hydrogen; hydroxy; chlorine; fluorine; an alkane having from 1 to 12 carbon atoms; an alkene having 2–4 carbon atoms; an arene having up to 10 carbon atoms, e.g., benzene or naphthalene, or a substituted arene in which one ring hydrogen may be replaced by a vinyl or allyl group, up to 8 ring hydrogens may be replaced by halogen, or up to 3 ring hydrogens may be replaced by nitro; a mono- or dialkylamino group having from 1 to 6 carbon atoms, including halogen-substituted alkylamino groups, e.g., those in which the ω-hydrogen is replaced by chlorine or bromine; an alkoxy having from 1 to 6 carbon atoms, including halogen-substituted, e.g., bromoalkoxy; and aryloxy having up to 10 carbon atoms in the aryl moiety thereof, e.g., phenoxy or naphthoxy, or an aryloxy substituted by chlorine, bromine or nitro; a 2-substituted ethenesulfonylaminoarene —N-H—Ar—SO$_2$CH=CH—X; aziridino; or morpholino;

Z is P, P$\longrightarrow$O, or P$\longrightarrow$S;

n is 1 or 2; and q is 1 when n is 2 and 2 when n is 1.

The Ar, X, R$_1$ and R$_2$ moieties of formula (C) are as specified above in connection with the compounds of Formulas (A) and (B).

More than one of the various substituents indicated may be provided on each of the above-noted moieties of the claimed compounds. For example, when R' on the sulfonamido-type compound is a phenyl-substituted alkene, the phenyl moiety may be unsubstituted or substituted by any one or a combination of the alkyl, halogen and nitro groups noted.

Conversion of the amino groups into acylamido groups such as N-acyl sulfonamido, phosphoramido, thiophosphoramido, phosphonamido, or thiophosphonamido groups in the β-X-ethenesulfonyl-substituted aminoarenes of the present invention tends to increase stability thereof against alkaline decomposition. This is particularly true in the case of fluorinated alkanesulfonamido compounds, because of the pronounced electronegativity of the fluorine atom. Perfluoroalkanesulfonamides of β-X-ethenesulfonyl-substituted aminoarenes, e.g., the trifluoromethanesulfonamides, are especially interesting since they are less irritating to humans than the corresponding aminoarenes. The anti-inflammatory effects of trifluoromethane sulfonamides is known and such compounds have been suggested as pharmaceuticals for the treatment of inflammatory conditions. The use of perfluoroalkanesulfonamides of aminoarenes as antimicrobial compounds with lower irritation potentials has not, however, previously been proposed.

The acylamides of the present invention may be employed as bioactives by exposing the plant or animal organisms to be controlled to the compounds utilizing techniques known in the art, e.g., those disclosed in the aforesaid copending Richter application. When, for example, the compounds are utilized as fungicides, nematocides, or phytotoxicants, they may be dispersed in soil or plant growth media and applied to plant systems in any convenient fashion. Application to the soil or growth media may be carried out by simply mixing with the media, by applying to the surface of the soil and thereafter mixing with the soil to the desired depth, or by employing a liquid carrier to accomplish the desired penetration and impregnation. The materials may be applied by conventional means, e.g., by power dusters, boom and hand sprayers, or spray dusters.

The exact amount of the active acylamido ingredient to be employed is dependent upon the particular application involved, the organism to be controlled, the medium in which the treatment is carried out, and the like. When, for example, the acylamido compounds are utilized as phytotoxicants and applied in foliar treatments, they are supplied in amounts of from about 1 to 50 or more pounds per acre. For similar purposes, when the active ingredient is applied to soil for the control or modification of the growth of germinant seeds, emerging seedlings and established vegetation, it may suitably be applied in amounts of from 0.01 to 25 or more pounds per acre. In such soil applications, it is desirable that the acylamido compound be applied in amounts of from about 0.01 to 5 pounds per acre.

The acylamido compounds hereof may be used alone or in combination with conventional liquid or solid adjuvants employed in the art. Such adjuvants may include solvents, diluents, extenders, carriers and conditioning agents to provide compositions in the form of finely divided particulate solids, granules, pellets, or aqueous dispersions, e.g., solutions or emulsions. Thus, the active ingredient may be used with adjuvants such as a finely divided particulate solid, an organic liquid, a wetting, dispersing or emulsifying agent, or any suitable combination thereof. Typical finely divided solid carriers and extenders which may be utilized in admixture with the acylamido bioactive compounds hereof to provide bioactive compositions include, e.g., the talcs, clays, pumice, silica, diatomaceous earth, quartz, fuller's earth, salt, sulfur, powdered cork, powdered wood, walnut flour, chalk, tobacco dust, charcoals, volcanic ash, pulverized urea-formaldehyde resins, polyurethanes and the like. Typical liquid diluents include, e.g., water, kerosene, Stoddard solvent, hexane, benzene, toluene, acetone, ethylene dichloride, xylene, alcohols, dimethylformamide, dimethylsulfoxide, Diesel oil, glycols and the like; or propellants like the Freons, etc.

In view of their excellent antimicrobial properties the acylamides of the β-X-ethenesulfonyl-substituted aminoarenes of the invention are additionally well suited for the protection of sensitive materials against attack by microorganisms such as bacteria, fungi, algae and the like. Such attack would otherwise take the form of complete or partial destruction, decrease in mechanical strength, discoloration by overgrowth, or the creation of odor or acidity or other undesirable manifestations. The bioactive materials hereof may also be incorporated in or combined with materials or products which may or may not themselves need protection against attack by microorganisms, but which will serve as vehicles for the destruction or inhibition of microorganisms which would otherwise grow on surfaces in direct contact or in proximity therewith. In such instances the antimicrobial action may be effected through the conveying action of separating fluid layers, e.g., water, air or the like. Examples of these latter applications of the bioactive compounds include the packaging of materials subject to microbial attack inside films or covering materials treated with the antimicrobial acylamides; shoes and clothing where the leather, plastic or textile materials have been treated with the antimicrobial acylamides; or other applications in which the purpose is to prevent the growth of odor producing or otherwise undesirable microorganisms on the skin.

The amount of active material necessary for protection varies considerably according to which specific acylamide is used, the type and number of organisms to be controlled, the growth conditions, the chemical environment, etc. A tropical climate will, for example, in general require a higher concentration of active material than a cold climate. In general, and although departures on both sides of the range may occasionally be desirable, the useful range is ordinarily from 0.1 to 5% by weight of the material to be protected or in the active vehicle as outlined above, and preferably between 0.2 and 3%. Of the large number of materials or products which can be protected through the use of the antimicrobial acylamides of the invention the following may be mentioned without limitation: cutting oils, drilling muds, embalming fluids, gasoline or fuels stored in steel tanks, household cleaners and soaps, detergent compositions, waxes and polishes; coatings and paints; rubbers and elastomers; plastics in various forms such as films, sheets, fibers, foams, extrusions, molded products; hides, leather; paper; wood and wood products; packaging films; clothing; textiles including both natural and/or synthetic blends; and cosmetic products such as lotions, ointments, bath oils, shampoos, and sprays.

The incorporation of the antimicrobial acylamides of the invention into these products can be carried out in various ways, as well known in the art. Thus, the active material may be added as a finely divided solid to fluid products, or ground with some of the material to be protected to a master batch which can be diluted, or it can be added in a solution, in emulsion, etc. Textiles, leather, paper and finished products may be treated by dipping in or spraying with solutions, emulsions or other dispersions, etc. Incorporation in plastics or elastomers can be by dry blending followed by suitable compounding, or introduction together with plasticizers, stabilizers, or other additives. In polyurethanes and other polymers formed from chemically reacting systems the active material can be added with one or several of the ingredients. In some cases there may be partial reaction between the active materials of the invention and reactive groups in the polymerizing mixture.

The antimicrobial acylamides of the invention are also useful in preventing the growth of slime and algae and the like in swimming pools, cooling towers and ponds, and in solutions used in paper manufacture, fiber board production and the like.

PREFERRED EMBODIMENTS OF THE INVENTION

Among the acylamides of $\beta$-X-ethenesulfonyl-substituted aminoarenes of the present invention are the acylamidoarenesulfonyl-substituted acrylonitrile, acrylamide and acrylate derivatives. It should, however, be understood that the electron-attracting moiety X defined in Formulas (A) and (B) above is not restricted to the —CN, —CONH$_2$ and —COOR$_1$ moieties and that the additional groups specified hereinabove are within the scope of the present invention. Indeed, the X substituent may be any electron-attracting or -withdrawing group and in some instances may, for example, even be —SO$_3$R$_1$.

Similarly, it should be understood that the $\beta$-X-ethenesulfonyl-substituted sulfinylamido (O=S=N), and the phosphin- (wherein Z is P), phosphor- and phosphon- (wherein Z is P→O), and thiophosphor- and thiophosphonamidoarenes (Z is P→S) of Formulas (B) and (C) above are within the scope of the present invention. A number of such compounds have shown outstanding activity against microorganisms.

Further, it should be understood that when R' or R'' contains a polymerizable group, both oligomers and polymers from the monomers of Formula (A) above, obtained by polymerization or copolymerization, may be provided. The polymerizable R' and R'' moieties may, for example, comprise ethene, 2-propene, o-, m-, or p-vinylbenzene or other vinyl groups. Such polymerizable vinyl-substituted arenes may be homopolymerized or copolymerized with other vinylic monomers to produce copolymers having increased solubility, compatibility, or the like. Comonomers thus useful include, for example, vinylpyrrolidone, acrylates or methacrylates such as hydroxyethyl and hydroxypropyl acrylate, octyl acrylate, vinyl sulfonate, etc. The comonomers can also be bioactive polymerizable substances themselves, e.g, CH$_2$=CHSO$_2$CH=CH.X; CH$_2$=CHOSO$_2$CH=CH.X; CH$_2$CHOOCO-SO$_2$CH=CH.X; CH$_2$=CHCH$_2$OOCOSO$_2$CH=CH.X; CH$_2$=CH.NHOSO$_2$CH=CH.X; CH$_2$=CHCH$_2$NHOSO$_2$CH=CH.X; CH$_3$OSO$_2$CH=CH-COOCH=CH$_2$; CH$_3$OSO$_2$CH=CHCOOCH$_2$CH=CH$_2$; CH$_3$SO$_2$CH=CHCOOCH$_2$CH$_2$OOCCH= CH$_2$, or the like. Such materials find limited application as bioactive materials, however.

Preferred among the acylamides of the present invention are:

the alkanesulfonamidobenzenesulfonylacrylonitriles, e.g., 3-(4-methanesulfonamidobenzenesulfonyl)acrylonitrile, 3-(4-ethanesulfonamidobenzenesulfonyl)acrylonitrile, 3-(4-propanesulfonamidobenzenesulfonyl)acrylonitrile, 3-(4-butanesulfonamidobenzenesulfonyl)acrylonitrile, 3-(hexadecanesulfonamidobenzenesulfonyl)acrylonitrile, 3-(4-dichloromethanesulfonamidobenzenesulfonyl)acrylonitrile, 3-(4-trichloromethanesulfonamidobenzenesulfonyl)acrylonitrile, 3-(3-trifluoromethanesulfonamidobenzenesulfonyl)acrylonitrile, 3-(3-perfluorooctanesulfonamido-6-chlorobenzenesulfonyl)acrylonitrile.

3-(4-phenylmethanesulfonamidobenzenesulfonyl)acrylonitrile, 3-(4-nitrobutanesulfonamidobenzenesulfonyl)acrylonitrile, and 3-(4-cyclohexanesulfonamidobenzenesulfonyl)acrylonitrile;

the alkene or phenyl-substituted alkene-sulfonamidobenzenesulfonyl acrylonitriles, e.g., 3-(4-ethenesulfonamidobenzenesulfonyl)acrylonitrile, 3[4-(2-phenylethenesulfonamido)benzenesulfonyl]acrylonitrile, 3-[4-(2-chloroethenesulfonamido)benzenesulfonyl]acrylonitrile, 3-[3-(1-chloroethenesulfonamido)benzenesulfonyl]acrylonitrile, 3-[2-(2-cyanoethenesulfonamido)benzenesulfonyl]acrylonitrile, 3-[4-(2-cyanoethenesulfonamido)benzenesulfonyl]acrylamide octanethiol 3-[4-(2-cyanoethenesulfonamido)naphthalenesulfonyl]acrylate, and 3-[4-(2-nitroethenesulfonamido)benzenesulfonyl]acrylonitrile;

the benzene or substituted benzene sulfonamidoarenesulfonyl acrylonitriles, acrylamides or acrylates, e.g., 3-(4-benzenesulfonamidobenzenesulfonyl)acrylonitrile,
3-[3-(benzenesulfonamido)-4-methylbenzenesulfonyl]acrylonitrile,
3-[4-(4-methylbenzenesulfonamido)benzenesulfonyl]acrylonitrile,
3-[4-(2-methylbenzenesulfonamido)benzenesulfonyl]acrylonitrile,
3-[(4-dodecylbenzenesulfonamido)benzenesulfonyl]acrylonitrile,
3-[4-(2,4,6-trimethylbenzenesulfonamido)benzenesulfonyl]acrylonitrile,
3-[4-(2,4,6-tri-isopropylbenzenesulfonamido)benzenesulfonyl]-acrylonitrile,
3-[4-(4-chloromethylbenzenesulfonamido)benzenesulfonyl]acrylonitrile, 3-[4-(4-vinylbenzenesulfonamido)benzenesulfonyl]acrylonitrile, poly-[4-(4-vinylbenzenesulfonamidophenyl) 2-cyanovinyl sulfone], poly-[(4-ethenesulfonamidophenyl) 2-cyanovinyl sulfone],
3-[4-(2,4-divinylbenzenesulfonamido)benzenesulfonyl]acrylonitrile,
3[4-(4-chlorobenzenesulfonamido)benzenesulfonyl]acrylonitrile,
3-[4-(4-fluorobenzenesulfonamido)benzenesulfonyl]acrylonitrile,
3-[4-(4-nitrobenzenesulfonamido)benzenesulfonyl]acrylonitrile,
3-[4-(3-nitrobenzenesulfonamido)benzenesulfonyl]acrylonitrile,
3-[4-(2-nitrobenzenesulfonamido)benzenesulfonyl]acrylonitrile,
3-[4-(2,4-dinitrobenzenesulfonamido)benzenesulfonyl]acrylonitrile,
3-[4-(4-chloro-3-nitrobenzenesulfonamido)benzenesulfonyl]acrylonitrile,
3-[4-(4-chloro-2-nitrobenzenesulfonamido)benzenesulfonyl]acrylonitrile,
3-[4-(2-hydroxy-3,5-dichlorobenzenesulfonamido)-benzenesulfonyl]-acrylonitrile,
3-[4-(4-hydroxy-3-carboxybenzenesulfonamido)-benzenesulfonyl] acrylonitrile,
3-[4-(3-carboxybenzenesulfonamido)benzenesulfonyl]acrylonitrile,
3-[4-(4-carbethoxybenzenesulfonamido)benzenesulfonyl]acrylonitrile,
3-[4-(4-cyanobenzenesulfonamido)benzenesulfonyl]acrylonitrile,
3-[4-(4-methoxybenzenesulfonamido)benzenesulfonyl]acrylonitrile,
3-[4-(3,4-dimethoxybenzenesulfonamido)benzenesulfonyl]acrylonitrile,
3-[4-(2,5-dimethoxybenzenesulfonamido)benzenesulfonyl]acrylonitrile,
3-[4-(4-acetamidobenzenesulfonamido)benzenesulfonyl]acrylonitrile,
N-4-(2-cyanoethenesulfonyl)phenyl N'-[3-(2-cyanoethenesulfonyl)-phenylsulfamoyl]benzamide,
3-[4-(4-dichlorocarbostyrenesulfonamido)benzenesulfonyl]acrylonitrile,
phenylene-1,3-bis-sulfon-4-(2-cyanoethenesulfonyl)anilide,
phenylene-1,3,5-tris-sulfon-4-(2-cyanoethenesulfonyl)anilide,
4,4'-N,N'-bis-4-(2-cyanoethenesulfonyl)phenylsulfamoyl diphenyl ether,
3-[4-(2-naphthalenesulfonamido)benzenesulfonyl]acrylonitrile,
3-[4-(2-naphthalenesulfonamido)-4-methyl-benzenesulfonyl] acrylonitrile,
3-[4-(5-dimethylaminonaphthalene-2-sulfonamido)-benzenesulfonyl]acrylonitrile,
naphthalene-2,6-bis-sulfon-[4-(2-cyanovinylsulfonyl)anilide],
3-(4-anthracenesulfonamidobenzenesulfonyl)acrylonitrile;
the thiadiazole-substituted sulfonamidobenzenesulfonyl acrylonitriles, e.g.,
3-[4-(2-acetamido-1,3,4-thiadiazole-5-sulfonamido)benzenesulfonyl]acrylonitrile;
the sulfinamido-substituted benzenesulfonyl acrylonitriles, acrylamides, and acrylates, e.g.,
3-(4-methanesulfinamidobenzenesulfonyl)acrylonitrile,
3-(3-dodecanesulfinamidobenzenesulfonyl)acrylamide,
3-(4-trichloromethanesulfinamidobenzenesulfonyl)acrylonitrile,
3-(4-benzenesulfinamidobenzenesulfonyl)acrylonitrile,
3-[4-(4-methylbenzenesulfinamido)benzenesulfonyl]acrylonitrile,
3-[4-(4-nitrobenzenesulfinamido)benzenesulfonyl]acrylonitrile,
3-[4-(3,4-dichlorobenzenesulfinamido)benzenesulfonyl]acrylonitrile, nonyl 3-[4-(3-chloro-4-nitrobenzenesulfinamido)-3-chlorobenzenesulfonyl]acrylate,
3-[4-(2-naphthalenesulfinamido)benzenesulfonyl]acrylonitrile,
3-[4-(5,6,7,8-tetrahydronaphthalenesulfinamido)-benzenesulfonyl]acrylonitrile;
the sulfenamido-substituted benzenesulfonyl acrylonitriles and acrylates, e.g.,
3-[(4-trichloromethanesulfenamido)benzensulfonyl]acrylonitrile,
butyl 3-[(4-trichloromethanesulfenamido)benzenesulfonyl] acrylate, and
3-[4-(4-nitrobenzenesulfenamido)benzenesulfonyl]acrylonitrile;
the sulfinylimido-substituted arenesulfonyl acrylonitriles, acrylamides and acrylates, e.g.,
3-(4-sulfinylimidobenzenesulfonyl)acrylonitrile,
3-[(3-sulfinylimido)-4-methylbenzenesulfonyl]acrylonitrile,
4-sulfinylimidophenyl 2-carbamoylamidovinyl sulfone,
cyclohexyl 3-(4-sulfinylimidobenzene)sulfonyl acrylate,
4-sulfinylimidophenyl 2-nitrovinyl sulfone,
3-sulfinylimido-4-methylphenyl 2-bromo-2-nitrovinyl sulfone,
4-sulfinylimidobenzenesulfonyl 2-(pentachlorobenzenesulfonyl)ethene,
bis-1,2-(4-sulfinylimido- 3-methylbenzenesulfonyl)ethene,
4-sulfinylimidophenyl 2-carboxyvinyl sulfone,
3-[4-sulfinylimido-3-nitronaphthalenesulfonyl]acrylonitrile,
4-sulfinylimidonaphthyl 2-carboxyvinyl sulfone;
3-[4-(3-fluorosulfonylbenzenesulfonamido)benzenesulfonyl] acrylonitrile;
the phosphoramidobenzenesulfonyl acrylonitriles, e.g., tris-N,N',N''-4(2-cyanoethenesulfonyl)phenylphosphoramide;
the chlorophosphoramidobenzenesulfonyl acrylonitriles or acrylates, e.g., chloro-di-[3-(2-cyanoethenesulfonyl)-5-methyl-anilido]phosphine oxide, and octyl 3-(4-dichlorophosphoramidobenzenesulfonyl)acrylate;

the 2-substituted ethenesulfonylamidoarenethiophosphoramidoarenesulfonylacrylonitriles, e.g., tris-4-(2-cyanoethenesulfonylanilido)phosphine sulfide;

the alkylamidophosphoramidobenzenesulfonylacrylonitriles, e.g., 4-di-heptylamidophosphoramidonaphthyl 2-cyanovinyl sulfone, bis-dimethylamido-4-(2-cyanoethenesulfonyl)anilidophosphine oxide, and bis-(2-chloroethyl)amido-di-4-(2-cyanoethenesulfonylanilido)phosphine oxide;

the hydroxy- or alkoxyphosphoramidobenzenesulfonylacrylonitriles or the corresponding nitro compounds, e.g., 4-(dihydroxyphosphoramidophenyl) 2-cyanovinyl sulfone, 4-diethoxyphosphoramidophenyl 2-trifluoromethylvinyl sulfone, 4-dimethoxyphosphoramidophenyl 2-nitrovinyl sulfone, and bis-(2,3-dibromopropoxy)-[4-(2-cyanoethenesulfonyl)anilido]-phosphine oxide;

the benzenephosphoramidobenzenesulfonylacrylonitriles, e.g., phenyl-di[4-(2-cyanoethenesulfonyl)anilido]phosphine oxide, and phenyl-di[4-(2-cyanoethenesulfonyl)anilido]phosphine sulfide;

the aziridinophosphoramidobenzenesulfonylacrylates, e.g., di-aziridino-4-(2-octylcarbonylethenesulfonylanilido)phosphine oxide;

and the morpholinophosphoramidobenzenesulfonyl acylamides, e.g, di-morpholino-4-(2-carbamoylethenesulfonylanilido)phosphine oxide.

Other compounds useful in the practice of the invention include:

2-cyanovinyl 4-phenylmethanesulfonamidophenyl sulfone, 2-carbamoylvinyl 3-sulfinylimido-4-methylphenyl sulfone, 2-(4-nitrophenoxycarbonyl)vinyl 4-sulfinylimido-3fluorophenyl sulfone, 2-cyanovinyl 4-butanesulfonamido-3-chlorophenyl sulfone, 2-cyanovinyl 4-hexanesulfonamido-2-nitrophenyl sulfone, 2-isopropylcarbonylvinyl 4-difluoromethanesulfonamido-3-fluorophenyl sulfone, tris-N,N',N''-4-(2-ethoxycarbonylethenesulfonyl)-3-fluorophenyl phosphoramide, and bis-(2,3-dibromopropoxy)- 4-(2-pentabromophenylethenesulfonyl)-2,6-dibromo-anilido phosphine oxide.

The preceding and other acylamides within the scope of the present invention may be prepared utilizing various routes, Thus, the corresponding substituted aminoarenes may be acylated to the desired acylamides with a sulfonyl chloride or with phosphorus trichloride, phosphoryl, sulfinyl or sulfenyl chloride, thiophosphoryl chloride, phosphorus pentachloride, or a phosphinic, phosphonic or thiophosphonic acid halide, depending upon the particular acylamide to be produced.

The sulfinylimido compounds are obtained by treating the β-X-ethenesulfonyl-substituted aminoarenes with thionyl chloride, preferably in a solvent.

It is well known that the use of tertiary amines, e.g., pyridine, triethylamine, collidine or the like, as acid acceptors in condensations of such acyl halides with primary or secondary amines, is quite effective. These tertiary amines may be used in the preparation of the substituted aminoarenes of the present invention as well. They should, however, be used with care since they tend to attack the substituted aminoarene product. On the the hand, triethylenediamine (which may also be termed 1,4-diaza[2.2.2]octane), a difunctional tertiary diamine, has been found particularly useful as an acid acceptor in the particular condensations hereof, such material not attacking the substituted aminoarenes to the same degree.

Alternatively, the desired acylamides may be prepared by reacting the substituted aminoarenes with an anhydride, e.g., trifluoromethanesulfonic anhydride, or a phosphinic or phosphonic acid, utilizing a condensing aid such as a carbodimide. Other methods so useful include treating the substituted aminoarenes with an organic sulfenyl chloride and oxidizing the resulting sulfenamides to the sulfinamides or sulfonamides. Sulfinamides can also be oxidized to the corresponding sulfonamides.

It is also possible to acylate the corresponding aminoarenesulfinic acids or salts in similar fashion and then react these acylated aminoarenesulfinic acids or salts with a vicinal dihalogenide. As described in the above-mentioned Richter and Tsolis patent, the unsaturated acylamides of the β-X-ethenesulfonyl-substituted aminoarenes may be thus directly formed. The required sulfinate reactants may also be obtained by similar acylation of the corresponding aminoarenesulfonic acids, conversion to the sulfonyl halides and reduction, for example with sodium sulfite and bisulfite, to the sulfinate.

The substituted aminoarenes to be acylated as aforesaid may be prepared employing methods known in the art. Suitable techniques for preparing such materials are described, for example, in the aforesaid copending Richter application and the Richter and Tsolis patent. By way of illustration, the said application specifically exemplifies the preparation of various of the β-X-ethenesulfonyl-substituted aminoarenes, including both acrylonitrile derivatives, e.g., 3-(4-aminobenzenesulfonyl)acrylonitrile (which may also be termed 2-cyanovinyl 4-aminophenyl sulfone) and 3-(4-acetamidobenzenesulfonyl)acrylonitrile (which may also be termed 2-cyanovinyl 4-acetamidophenyl sulfone), and acrylamides, e.g., 3-(p-toluenesulfonyl)acrylamide. Other of the β-X-ethenesulfonyl-substituted aminoarenes may be similarly prepared, e.g., 3-(4-aminobenzenesulfonyl)acrylamide may be made from 3-(4-aminobenzenesulfonyl)acrylonitrile.

The corresponding esters, which may be acylated to those compounds of the invention wherein X equals $COOR_1$, may be conventionally made from these sulfonylacrylamides by boiling under reflux with alcohols, e.g., methanol, ethanol, trifluoroethanol, phenol, cyclohexanol or the like, in the presence of a catalyst such as sulfuric acid. In this manner, the 2-carbalkoxyvinyl aminophenyl sulfones and analogous compounds may be prepared.

Alternatively, it may sometimes be more convenient to prepare the amides, esters or other X-ethenesulfonyl-substituted aminoarenes to be acylated to the compounds of the invention, directly from the corresponding nitro compounds followed by reduction thereof. Yet a further alternative involves hydrolyzing the 2-cyanovinyl nitroaryl sulfones to the corresponding 2-carboxyvinyl nitroaryl sulfones, and converting the carboxyl function to the desired derivative by direct esterification or other conventional techniques, followed by reduction.

The methods of making and using various preferred embodiments of the acylamides hereof are illustrated in the following examples. Unless otherwise indicated, all parts and percentages specified in the examples are given by weight, and all temperatures are in degrees Celsius.

EXAMPLE 1:
3-(4-METHANESULFONAMIDOBENZENESULFONYL)ACRYLONITRILE 23 grams (0.2 mol) of methanesulfonyl chloride ($CH_3SO_2Cl$) are dissolved in 600 milliliters of chloroform, and 42 grams (0.2 mol) of 3-(4-aminobenzenesufonyl)acrylonitrile, prepared as described in copending application Ser. No. 228,410 filed Feb. 22, 1972, are added with stirring and cooling in an ice bath followed portionwise by a solution of 16 g (0.2 mol) of pyridine in 200 ml of pyridine. The reaction mixture is allowed to reach room temperature and is thereafter left at about 20° C for about 48 hours. The solution is filtered and then washed with water, a 5% solution of HCl in water, a 5% sodium bicarbonate solution in water, and water, in sequence.

The chloroform layer is separated from the water in a separatory funnel, dried over anhydrous sodium sulfate, filtered, and evaporated to a small volume. Petroleum ether is added to this solution. A yellowish solid separates which, after recrystallization from ethanol, gives a solid having a melting point of 219°–222° C. This is 3-(4-methanesulfonylamidobenzenesulfonyl)acrylonitrile:

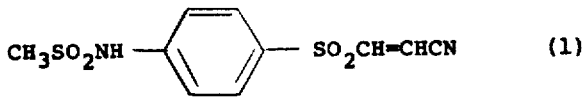

(1)

EXAMPLE 2:
3-(4-ETHANESULFONAMIDOBENZENESULFONYL)ACRYLONITRILE 42 grams (0.2 mol) of 3-(4-aminobenzenesulfonyl)-acrylonitrile are added to a cooled solution of 26 g (0.2 mol) of ethanesulfonyl chloride ($CH_3CH_2SO_2Cl$) in 600 ml of chloroform with stirring. 16 g (0.2 mol) of pyridine in 200 ml of chloroform are added portionwise. The temperature is allowed to rise to about 20° C and the reaction mixture is left at this temperature for 48 hours with stirring. Unreacted aminobenzenesulfonylacrylonitrile is recovered by filtration and the filtrate is then worked up as in Example 1. A yellowish solid with a melting point of 177°–180° C is obtained. This is 3-(4-ethanesulfonamidobenzenesulfonyl)acrylonitrile:

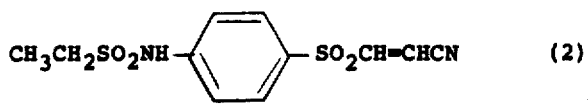

(2)

EXAMPLE 3:
3-(4-BUTANESULFONAMIDOBENZENESULFONYL)ACRYLONITRILE 8.2 grams (0.04 mol) of 3-(4-aminobenzenesulfonyl) acrylonitrile are dissolved in 100 ml of dioxane and 3.3 ml (0.04 mol) of pyridine are added. 6.3 g (0.04 mol) of butanesulfonyl chloride ($CH_3CH_2CH_2CH_2SO_2Cl$) dissolved in 50 ml of dioxane are added in one portion to the first solution and the reaction mixture is allowed to stand for 48 hours at room temperature, then heated to 85° C for one hour. After cooling, the reaction mixture is poured into 700 ml of ice-cold water and the separated solid is recovered by filtration and drying.

The solid is dissolved in ethanol, decolorized with charcoal and recrystallized. After a second decolorization and recrystallization a solid having a melting point of 153.5°–155.5° C is obtained. The product is 3-(4-butanesulfonamidobenzenesulfonyl)acrylonitrile:

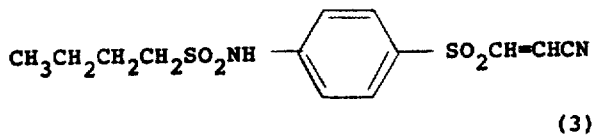

(3)

EXAMPLE 4:
3-(HEXADECANESULFONAMIDOBENZENESULFONYL)ACRYLONITRILE 6.3 grams (0.03 mol) of 3-(4-aminobenzenesulfonyl) acrylonitrile is dissolved in 60 ml of dioxane and 4 ml (about 0.03 mol) triethylamine are added. A clear solution results. 9.8 grams (0.03 mol) of hexadecanesulfonyl chloride is added to a mixture of 50 ml of dioxane and 20 ml of acetone. Only partial dissolution occurs, but when the slurry is added to the aminobenzenesulfonylacrylonitrile-triethylamine solution a clear solution is obtained. After about 5 minutes a precipitate (of triethylamine hydrochloride) begins to form.

After standing at room temperature for 16 hours the amine hydrochloride is filtered off and the filtrate is mixed with 500 ml of water. An emulsion is formed which is extracted with 300 ml of chlorofrom. After standing two days a yellow chloroform layer separates which is treated with anhydrous magnesium sulfate to remove traces of water, and is then evaporated to give a yellow-brown oil. Treatment with ethanol and recovery gives a yellow, somewhat soft, powdery solid. This is

(4)

EXAMPLE 5:
3-(4-TRIFLUOROMETHANESULFONAMIDOBENZENESULFONYL)ACRYLONITRILE

A mixture of 20.8 g (0.1 mol) of 3-(4-aminobenzenesulfonyl)acrylonitrile and 11.2 g (0.1 mol) of 1,4-diazabicyclo-[2.2.2]-octane in 500 ml of chloroform is stirred at about 15°–25° C while trifluoromethanesulfonic acid anhydride is slowly added thereto. The reaction mixture is stirred for an additional hour and is then washed several times with dilute HCl and water, filtered, dried over anhydrous magnesium sulfate, and evaporated to dryness. The recovered solid can be recrystallized from ethanol to give 3-(4-trifluorosulfonamidobenzenesulfonyl)acrylonitrile (or 2-cyanovinyl 4-trifluoromethanesulfonamidophenyl sulfone):

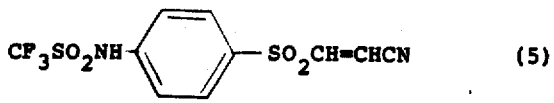

(5)

EXAMPLE 6: 3-(4-TRIFLUOROMETHANESULFONAMIDONAPHTHALENESULFONYL)ACRYLONITRILE 25.8 g (0.1 mol) of 2-cyanovinyl 4-aminonaphthyl sulfone (or 3-(4-aminonaphthalenesulfonyl)acrylonitrile are prepared by reacting an aqueous solution of 4-acetamidonaphthalenesulfinate, buffered with sodium acetate, with 2,3-dichloropropionitrile in accordance with the method described in U.S. Pat. No. 3,541,119 owned by the assignee of the present invention, and hydrolyzing the product with dilute HCl to remove the acetyl group. The resulting material is treated with trifluoromethanesulfonic anhydride in the manner described in Example 5, producing 2-cyanovinyl 4-trifluoromethanesulfonamidonaphthyl sulfone (3-(4-trifluoromethanesulfonamidonaphthalenesulfonyl)acrylonitrile:

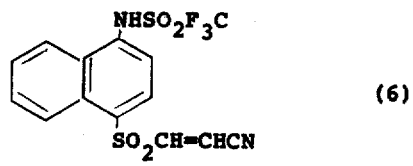

(6)

EXAMPLE 7: 2-CYANOVINYL 4-AMINO-3-NITROPHENYL SULFONE 3-(4-acetamidobenzenesulfonyl)acrylonitrile, prepared as described in the aforesaid U.S. Pat. No. 3,541,119, is nitrated at about room temperature in a mixture of nitric acid and concentrated sulfuric acid for about two hours, and thereafter drowned in ice water. The 2-cyanovinyl 4-acetamido-3-nitrophenyl sulfone recovered is hydrolyzed in a mixture of dilute hydrochloric acid and ethanol to give 2-cyanovinyl 4-amino-3-nitrophenyl sulfone. 25.3 g (0.1 mol) of this material is carefully dried and is dispersed in 500 ml chloroform and 11.2 g 1,4-diaza-[2.2.2]octane is added thereto. A chloroform solution of difluoromethanesulfonyl chloride in about 10% excess is added to the stirred mixture of the substituted aminoarene and the acid acceptor at 50° C. The mixture is stirred at this temperature for 2 hours and is then maintained at room temperature for 2 days. After treatment with dilute HCl to remove the tertiary amine and unreacted starting material, and evaporation of the solvent, a crude material is obtained which is purified by recrystallization, giving 2-cyanovinyl 4-difluoroacetamido-3-nitrophenyl sulfone:

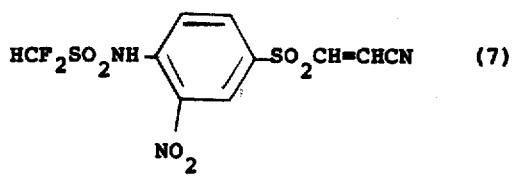

(7)

EXAMPLE 8: 2-CARBETHOXYVINYL 3-PERFLUOROOCTANESULFONAMIDO-5-CHLOROPHENYL SULFONE 2-carbethoxyvinyl 3-amino-5-chlorophenyl sulfone is prepared by reacting sodium 3acetamido-5-chlorobenzenesulfinate in aqueous ethanol solution, in the presence of potassium acetate, with 2,3-dichloropropionamide. The resulting 2-carboxyamidovinyl 3-acetamido-5-chlorophenyl sulfone is hydrolyzed with dilute hydrochloric acid to give 2carboxyamidovinyl 3-amino-5-chlorophenyl sulfone. The dried solid is boiled with ethanol under reflux for 2 hours in the presence of concentrated sulfuric acid. After drowning in water and neutralization 2-carbethoxyvinyl 3-amino-5-chlorophenyl sulfone is obtained.

5.8 g (0.02 mol) of the dried material is dissolved in 100 ml of dioxane, and 2.3 (0.02 mol) of 1,4-diaza[2.2.2]octane is added thereto. The solution is stirred and 10.4 g (0.02 mol) of perfluorooctane sulfonyl chloride in 100 ml dioxane is slowly added. The reaction mixture is heated at 50° C for 4 hours and the sulfonamide is recovered, affording the desired 2-carbethoxyvinyl 3-perfluorooctanesulfonamido-5-chlorophenyl sulfone:

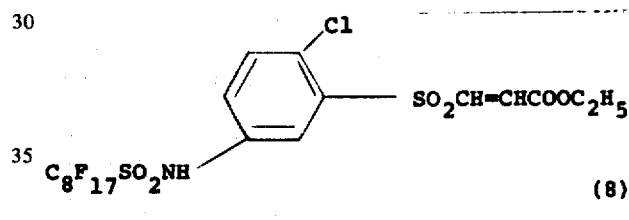

(8)

EXAMPLE 9: 3-(4-ETHENESULFONAMIDOBENZENESULFONYL)ACRYLONITRILE 10.4 grams (0.05 mol) of 3-(4-aminobenzenesulfonyl) acrylonitrile are dissolved in 200 ml of acetone and filtered to remove a small amount of insoluble material. The solution is cooled to −10° C to −20° C in an acetone-solid carbon dioxide bath. A solution of 8.1 g (0.05 mol) of 2-chloroethanesulfonyl chloride in 50 ml of acetone is similarly cooled. The aromatic amine solution is slowly added to the sulfonyl chloride solution while the latter is in the cooling bath. When about a third of the amine solution has been added, 14 ml (0.1 mol) of triethylamine is mixed into the remaining amine solution and the resulting mixture is slowly fed into the sulfonyl chloride reaction mixture. A light, flocculated precipitate begins to form.

The reaction mixture is left in the cooling bath until the dry ice has melted (about ¾ hour). The temperature is then allowed to rise to room temperature. The triethylamine hydrochloride thus formed is filtered off and 5 ml of 5 N HCl are added. After cooling and crystallizing a yellow, strong smelling solid is recovered. The product is

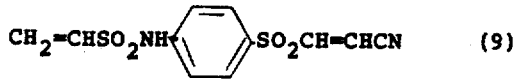

(9)

EXAMPLE 10:
3-[4-(2-PHENYLETHENESULFONAMIDO)BENZENESULFONYL]ACRYLONITRILE 4.1 grams (0.02 mol) of 2-phenylethenesulfonyl chloride (β-styrenesulfonyl chloride, $C_6H_5CH=CHSO_2Cl$) are dissolved in 50 ml of chloroform; 4.2 g (0.02 mol) of 3-(4-aminobenzenesulfonyl)acrylonitrile are added, followed by 1.6 g (0.02 mol) of pyridine. The reaction mixture is stirred at room temperature for 6 hours, and is then refluxed on a steam bath for 10 minutes. After filtration, the chloroform solution is washed with water, 5% HCl, and water, in that order.

The chloroform layer thus separated is dried over anhydrous sodium sulfate, filtered and evaporated. A solid with a melting point of 197°–200° C is obtained. The product is 3-[4-(2-phenylethenesulfonamido)benzenesulfonyl]acrylonitrile:

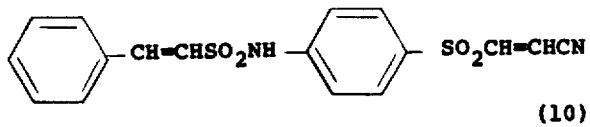

(10)

EXAMPLE 11:
3-(4-BENZENESULFONAMIDOBENZENESULFONYL)ACRYLONITRILE 4.2 grams (0.02 mol) benzenesulfonyl chloride, 4.2 g (0.02 mol) of 3-(4-aminobenzenesulfonyl)acrylonitrile, and 1.6 g (0.02 mol) of pyridine are reacted in 60 ml chloroform in accordance with the procedure described in Example 1. After washing with water, dilute hydrochloric acid, dilute sodium bicarbonate solution, and water, in that order, the chloroform layer yields a solid having a melting point of 158°–162° C. The product is 3-(4-benzene-sulfonamidobenzenesulfonyl)acrylonitrile:

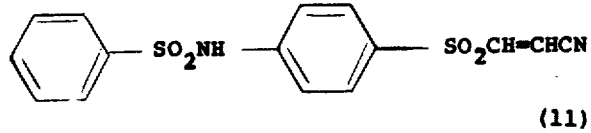

(11)

EXAMPLE 12:
3-(3-BENZENESULFONAMIDO-4-METHYL BENZENESULFONYL)ACRYLONITRILE 22.2 g (0.1 mol) of 3-(4-methyl-3-aminobenzenesulfonyl) acrylonitrile are dissolved in 150 ml dioxane, and 8 ml pyridine is added thereto. A solution of 17.6 g (0.1 mol) of benzenesulfonyl chloride is added dropwise, with stirring, at room temperature. A slight exotherm is obtained. The reaction mixture is stirred for 2 hours and is then left at room temperature for 16 hours. The solution is then poured into a stirred ice water mixture (3 liters). The recovered solid is 3-(3-benzenesulfonamido-4-methyl benzenesulfonyl)acrylonitrile:

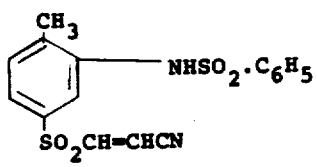

(35)

EXAMPLE 13:
3-[4-(4-METHYLBENZENESULFONAMIDO)BENZENESULFONYL]ACRYLONITRILE 4.9 grams (0.025 mol) of para-toluenesulfonyl chloride, and 4.5 g (0.025 mol) of 3-(4-aminobenzenesulfonyl) acrylonitrile in chlorofrom are reacted for 48 hours at room temperature in the presence of 2.2 ml (0.027 mol) of pyridine, and the reaction mixture is worked up as in Example 1. The product, recrystallized from ethanol, and having a melting point of 172°–175° C, is 3-[4-(4-methylbenzenesulfonamido)benzenesulfonyl]acrylonitrile:

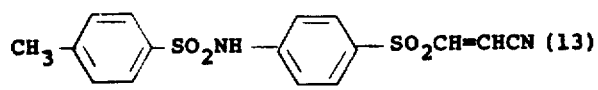

EXAMPLE 14:
3-[4(4-methylbenzenesulfonamido)benzenesulfonyl]acrylamide 22.6 g (0.1 mol) of 3-(4-aminobenzenesulfonyl)acrylamide, prepared by hydrolysis of 3-(4-aminobenzenesulfonyl acrylonitrile with a 1:1 molar mixture of concentrated sulfuric acid and water, is dissolved in dimethylformamide (100 ml), and 14.5 ml triethylamine (0.1 mol) are added thereto. A solution of p-toluenesulfonyl chloride (19.1 g, 0.1 mol) in 50 ml dimethylformamide is added dropwise at room temperature, and the reaction mixture is left undisturbed for 16 hours. The product is recovered by precipitation with water and recrystallization from ethanol. There is thus produced 3-[4-(4-methylbenzenesulfonamido)-benzenesulfonyl]acrylamide:

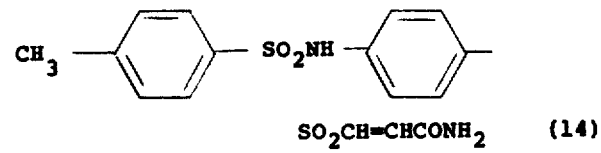

EXAMPLE 15: ETHYL 3-[4-(4-METHYLBENZENESULFONAMIDO)-BENZENESULFONYL]ACRYLATE 25.5 g (0.1 mol) of ethyl 3-(4-aminobenzenesulfonyl) acrylate, prepared by refluxing 3-(4-aminobenzenesulfonyl)acrylamide in an excess of absolute ethanol and in the presence of concentrated sulfuric acid as a condensing agent, are dissolved in acetone (100 ml). 14.5 ml of triethylamine (0.1 mol) are added as an HCl acceptor. A solution of p-toluenesulfonyl chloride (19.1 g, 0.1 mol) in 50 ml acetone is added dropwise at room temperature. The reaction mixture is left for 12 hours and is then poured into ice water. The precipitated solid is recovered by filtration, dried and recrystallized from ethanol, giving ethyl 3-[4-(4-methylbenzenesulfonamido)benzenesulfonyl]acrylate:

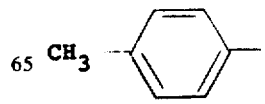
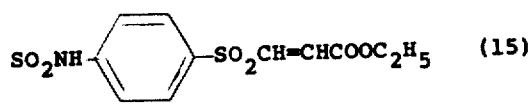

EXAMPLE 16: 3-[4-(2-METHYLBENZENESULFONAMIDO)BENZENESULFONYL]ACRYLONITRILE 4.2 grams (0.02 mol) of 3-(4-aminobenzenesulfonyl)-acrylonitrile are dispersed in 60 ml of dichloromethane containing 1.6 g (0.02 mol) of pyridine. The mixture is stirred and 3.8 g (0.02 mol) of ortho-toluenesulfonyl chloride are added with cooling. The reaction mixture is then mantained at room temperature for 48 hours, and after filtration the dichloromethane layer is washed and worked up as described in Example 1.

Petroleum ether is added to the concentrated solution and a yellow colored solid crystallizes. After recrystallization from ethanol a solid having a melting point of 164°–166° C is obtained. The product is 3-[4-(2-methylenebenzenesulfonamido)benzenesulfonyl]acrylonitrile:

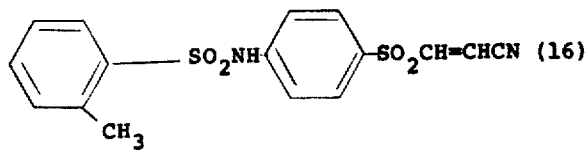

EXAMPLE 17: 3-[(4-dodecylbenzenesulfonamido)benzenesulfonyl]acrylonitrile 6.9 grams (0.02 mol) of 4-dodecylbenzenesulfonyl chloride dissolved in 100 ml acetate are added, at room temperature, to a stirred solution of 3-(4-aminobenzenesulfonyl)acrylonitrile (4.2 g, 0.02 mol) and 3ml (0.02 mol) of triethylamine in 150 ml acetone. The mixture is permitted to stand overnight. 3-[(4-dodecylbenzenesulfonamido)benzenesulfonyl]acrylonitrile is recovered as a soft, fine yellow powder:

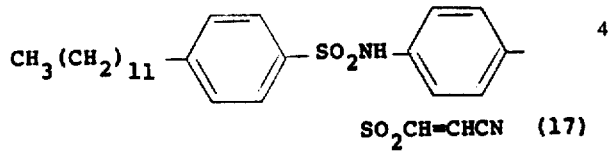

EXAMPLE 18: 3-[4-(2,4,6-TRIMETHYLBENZENESULFONAMIDO)BENZENESULFONYL]ACRYLONITRILE

A solution of 6.6 g (0.03 mol) of 2,4,6-trimethylbenzenesulfonyl chloride in 50 ml chloroform is added at room temperature to a stirred slurry of 6.3 g (0.03 mol) of 3-(4-aminobenzenesulfonyl)acrylonitrile in 100 ml chloroform, the slurry additionally containing 4 ml (0.03 mol) triethylamine, portionwise over a five minute period. After 3 hours stirring the reaction mixture is filtered. The chloroform solution is thereafter washed with water, dilute hydrochloric acid, and water, in that order, separated from the water layer, dried over anhydrous magnesium sulfate and evaporated. The recovered 3-[4-(2,4,6-trimethylbenzenesulfonamido)benzenesulfonyl]acrylonitrile has the formula:

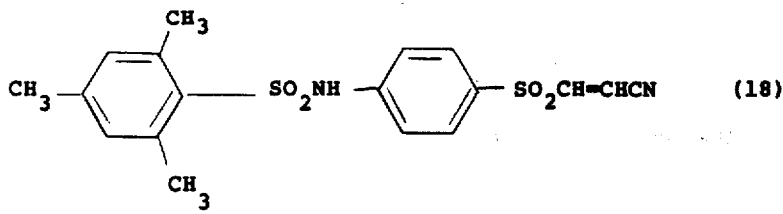

EXAMPLE 19: 3-[4-(2,4,6-TRI-ISOPROPYLBENZENESULFONAMIDO)BENZENESULFONYL]acrylonitrile a solution of 9.1 g (0.03 mol) of 2,4,6-tri-isopropylbenzenesulfonyl chloride in 50 ml dioxane is added at room temperature to a solution of 6.3 g (0.03 mol) of 3-(4-aminobenzenesulfonyl)acrylonitrile in 150 ml dioxane, the dioxane solution additionally containing 3 ml (0.03 mol) of pyridine. After 8 hours the reaction mixture is filtered and evaporated and a tannish solid consisting of 3-[4-(2,4,6-tri-isopropylbenzenesulfonamido)benzenesulfonyl]acrylonitrile is obtained:

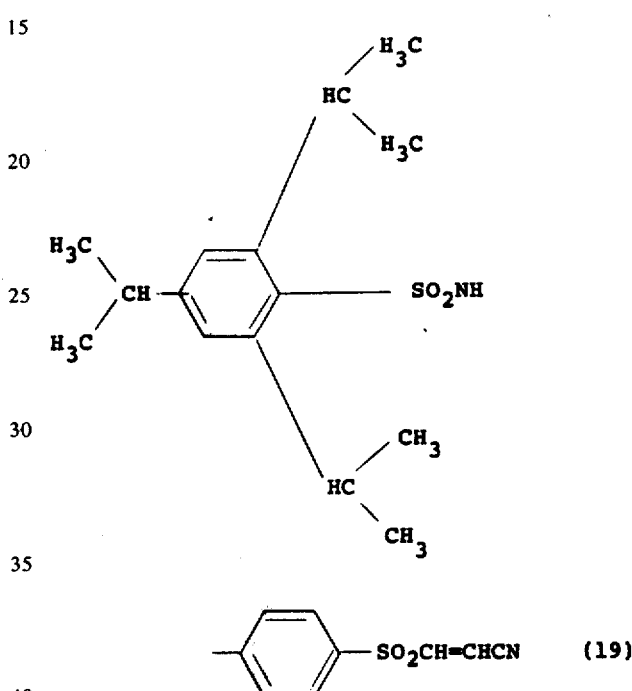

EXAMPLE 20: 3-[4-(4-CHLOROBENZENESULFONAMIDO)BENZENESULFONYL]ACRYLONITRILE

To a stirred and cooled mixture of 21 grams (0.1 mol) of 3-(4-aminobenzenesulfonyl)acrylonitrile and 8 g (0.1 mol) pyridine in 600 ml dichloromethane is added a solution of 21 g (0.1 mol) para-chlorobenzenesulfonyl chloride in 200 ml dichloromethane. The reaction mixture is maintained at room temperature for 48 hours. After work-up as described in Example 1 and recrystallization from ethanol a solid is obtained having a melting point of 167°–169° C. The product is 3-[4-(4-chlorobenzenesulfonamido)benzenesulfonyl]acrylonitrile:

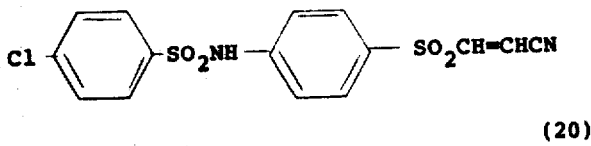

EXAMPLE 21: 3-[4-(4-FLUOROBENZENESULFONAMIDO)BENZENESULFONYL]ACRYLONITRILE 24 g (0.12 mol) of 3-(4-aminobenzenesulfonyl)acrylonitrile are dissolved in 200 ml acetone. 23.4 g (0.12 mol) of a solution of p-fluorobenzenesulfonyl chloride in 100 ml acetone are added thereto in several portions at room temperature, followed by 28 ml (0.12 mol) tributylamine. After standing for 8 hours at room temperature the reaction mixture is poured into 1 liter of water to separate the reaction product, which is then taken up in chloroform, and treated as described hereinabove to give 3-[4-(4-fluorobenzenesulfonamido)-benzenesulfonyl]acrylonitrile:

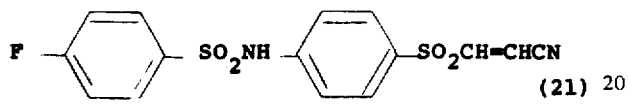

(21)

EXAMPLE 22: ISOMERS OF NITROBENZENESULFONAMIDOBENZENESULFONYL ACRYLONITRILE 4.2 g (0.02 mol) of 3-(4-aminobenzenesulfonyl)acrylonitrile and 4.43 g (0.02 mol) of p-nitrobenzenesulfonyl chloride are dissolved in 60 ml dioxane, and 1.65 g (0.02 mol) of pyridine are added thereto. After 24 hours at room temperature the reaction mixture is refluxed for 2 hours on a steam bath and, after cooling, poured into 200 ml ice water. The crystalline product thus separated is dried and recrystallized from ethanol, giving a product having a melting point of 178°–182°C. The product is 3-[4-(4-nitrobenzenesulfonamido)benzenesulfonyl]acrylonitrile:

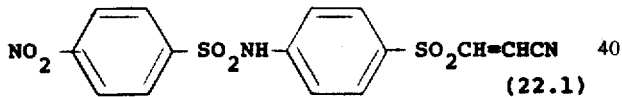

(22.1)

By essentially the same procedure, but using 3-nitrobenzenesulfonyl chloride instead of the para compound and carrying out the reaction first at room temperature for 6 hours and thereafter at reflux for one hour, there is obtained a yellow solid having a melting point of 156°–158° C, viz., 3-[4-(3-nitrobenzenesulfonamido)benzenesulfonyl]acrylonitrile:

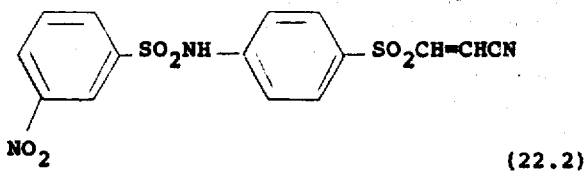

(22.2)

The ortho isomer, 3-[4-(2-nitrobenzenesulfonamido)benzenesulfonyl]acrylonitrile, having a melting point of 141°–143.5° C is obtained by the same procedure as above except that the reaction mixture is not heated under reflux, and 2-nitrobenzenesulfonyl chloride is utilized as the sulfonyl chloride reactants. The ortho isomer has the following formula:

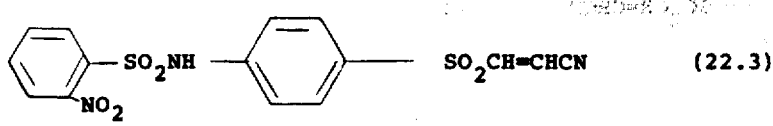

(22.3)

EXAMPLE 23: DINITRO- AND CHLORONITRO-BENZENESULFONAMIDO-BENZENESULFONYLACRYLONITRILES

By reacting solutions of 3-(4-aminobenzenesulfonyl)acrylonitrile in acetone with the corresponding sulfonyl chlorides (and employing triethylamine, pyridine, and triethylamine as the respective HCl acceptors), the following sulfonamides are prepared:

3-[4-(2,4-dinitrobenzenesulfonamido)benzenesulfonyl]acrylonitrile:

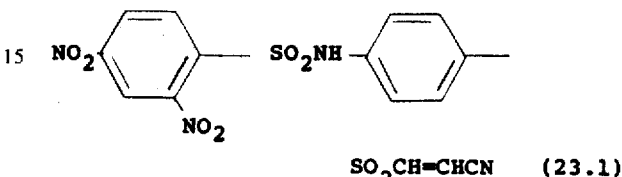

(23.1)

3-[4-(4-chloro-3-nitrobenzenesulfonamido)benzenesulfonyl]acrylonitrile:

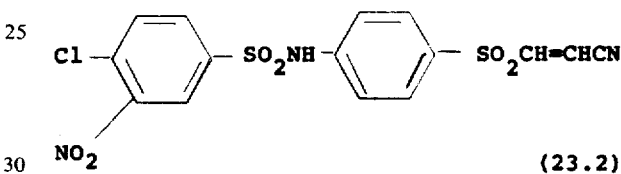

(23.2)

3-[4-(4-chloro-2-nitrobenzenesulfonamido)benzenesulfonyl]acrylonitrile:

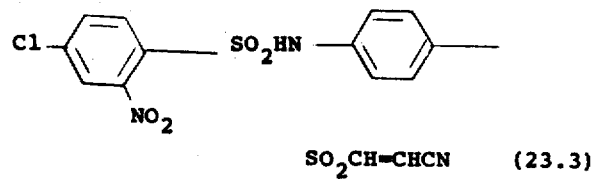

(23.3)

EXAMPLE 24: 3-[4-(3,5-DICHLORO-2-HYDROXYBENZENESULFONAMIDO)-BENZENESULFONYL]ACRYLONITRILE

To a solution of 4.2 g (0.02 mol) of 3-(4-aminobenzenesulfonyl)acrylonitrile in 40 ml of dioxane (containing 1.6 ml pyridine) is added a solution of 5.3 g (0.02 mol) of 2-hydroxy-3,5-dichlorobenzenesulfonyl chloride in 15 ml dioxane. The second solution is slowly added to the first over a 10-minute period. The reaction mixture (which takes on an orange color) is stirred for 2 hours at room temperature and then left for 16 hours. Water is added and the precipitate is filtered off and dried, giving the pink, fluffy 3-[4-(3,5-dichloro-2-hydroxy benzenesulfonamido)-benzenesulfonyl]acrylonitrile:

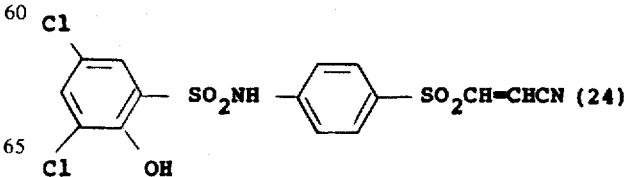

EXAMPLE 25:
3-[4-(4-HYDROXY-3-CARBOXYBENZENESULFONAMIDO)-BENZENESULFONYL]ACRYLONITRILE

The noted compound

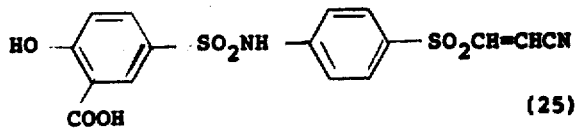

(25)

is prepared by dissolving 10.4 grams (0.05 mol) of 3-(4-aminobenzenesulfonyl)acrylonitrile and 14 g (0.05 mol + 15% excess) of 4-hydroxy-3-carboxybenzenesulfonyl chloride in 200 ml acetone, cooling in an ice bath and slowly adding thereto 8 ml (0.055 mol) of triethylamine diluted with 25 ml acetone. After filtration and evaporation of the acetone the remaining semi-solid is dissolved in dimethylformamide, dispersed in water and the emulsion extracted with chloroform. After work-up the above sulfonamide is recovered.

EXAMPLE 26:
3-[4-(3-CARBOXYBENZENESULFONAMIDO)-BENZENESULFONYL]ACRYLONITRILE 2.1 g (0.01 mol) of 3-(4-aminobenzenesulfonyl)acrylonitrile are dissolved in 100 ml dioxane, and 2 ml of pyridine are added thereto. A solution of 2.21 g (0.01 mol) of 3-carboxybenzenesulfonyl chloride in 50 ml dioxane is added portionwise at room temperature and the reaction mixture is held overnight. After filtering and mixing the filtrate with about 4 volumes of water the mixture is left at room temperature for 5 days. White flocs separate which are recovered by filtration and dried, giving 3-[4-(3-carboxybenzenesulfonamido)-benzenesulfonyl]acrylonitrile:

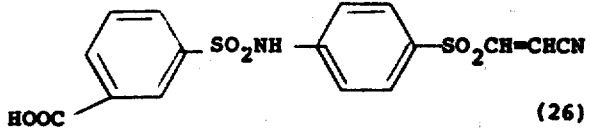

(26)

EXAMPLE 27:
3-[4-(4-CARBETHOXYBENZENESULFONAMIDO)BENZENESULFONYL]ACRYLONITRILE 6.3 grams (0.03 mol) of 3-(4-aminobenzenesulfonyl)acrylonitrile are dissolved in 70 ml of acetone, and 30 ml water are added thereto. Sodium bicarbonate (2.6 g, 0.03 mol) is added with stirring, followed by a solution of 7 g (0.03 mol) of 4-carbethoxybenzenesulfonyl chloride in 30 ml acetone. The reaction mixture is stirred overnight, filtered and the filtrate diluted with 750 ml water. The dark, cream-colored solid which separates and which is recovered by filtration and drying constitutes 3-[4-(4-carbethoxyxbenzenesulfonamido)benzenesulfonyl]acrylonitrile:

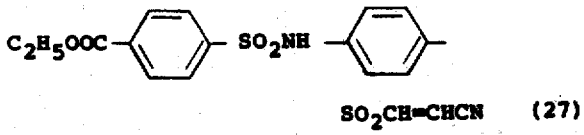

(27)

EXAMPLE 28:
3-[4-(4-METHOXYBENZENESULFONAMIDO)-BENZENESULFONYL]ACRYLONITRILE 6.3 g (0.03 mol) of 3-(4-aminobenzenesulfonyl) acrylonitrile are dissolved in 100 ml dioxane. 3 ml of pyridine followed by a solution of 6.3 g (0.03 mol) of 4-methoxybenzenesulfonyl chloride in 30 ml of dioxane are thereafter added thereto at room temperature. The reaction mixture is left overnight, then filtered, evaporated and extracted with chloroform. After work-up of the chloroform solution and purification from ethanol a tan solid is obtained. The product is 3-[4-(4-methoxybenzenesulfonamido)benzenesulfonyl]a-crylonitrile:

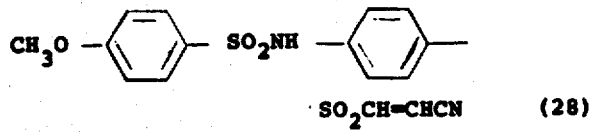

(28)

EXAMPLE 29:
dimethoxybenzenesulfonamidobenzenesulfonylacrylonitriles

3-[4-(3,4-dimethoxybenzenesulfonamido)benzenesulfonyl]acrylonitrile:

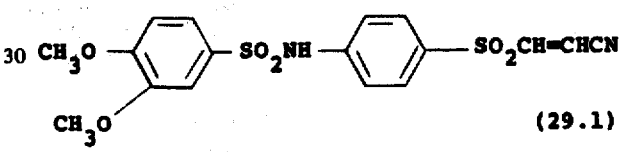

(29.1)

or 3-[4-(2,5-dimethoxybenzenesulfonamido)benzenesulfonyl]acrylonitrile:

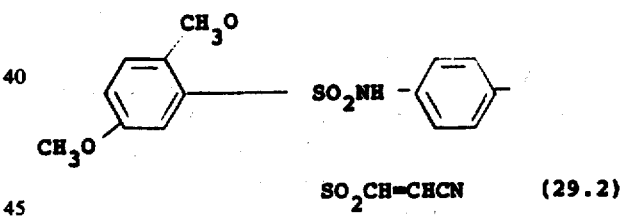

(29.2)

are prepared by reaction of mixtures of 3-(4-aminobenzenesulfonyl) acrylonitrile and the corresponding sulfonyl chloride. The reactions are carried out in acetone solutions in the presence of triethylamine, the mixtures being maintained at room temperature for several hours, heated briefly to 60° C, and recovered and worked-up as aforesaid.

EXAMPLE 30:
3-[4-(4-ACETAMIDOBENZENESULFONAMIDO)-BENZENESULFONYL]ACRYLONITRILE

To a dispersion of 3.6 grams (0.017 mol) of 3-(4-aminobenzenesulfonyl)acrylonitrile and 4.7 g (0.02 mol) of 4-acetamidobenzenesulfonyl chloride in 50 ml of chloroform is added 2 ml of pyridine. There is an exothermic reaction and an upper yellow, oily layer is formed. After 48 hours at room temperature 50 ml of chloroform are added, followed by water. The water and chloroform layers are separated and discarded, and the oily layer is shaken with water, separated and then dissolved in 30 ml ethanol. After cooling, crystals are recovered having a melting point of 204°–205° C and consisting of 3-[4-(4-ACETAMIDOBENZENESUL- FONAMIDO)BENZENESULFONYL]acrylonitrile:

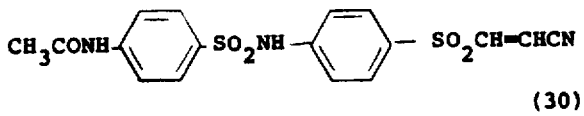

(30)

allowed to stand at room temperature for 4 days with occasional stirring. It is then poured into 400 ml of water and the oily suspension stirred for 5 hours after which the oil solidifies. After drying, the pink solid obtained is N.N'-bis-[4-(2-cyanoethenesulfonyl)-phenyl]-1,3-phenylenesulfonamide:

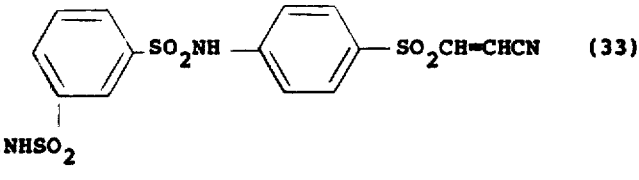

(33)

EXAMPLE 31:
N'-4-(2-CYANOETHENESULFONYL)PHENYL N''-3-(2-CYANOETHENESULFONYL)PHENYL- SULFAMOYLBENZAMIDE

To a solution of m-chlorosulfonylbenzoyl chloride (2.4 g, 0.01 mol) in 50 ml chloroform 3.6 g (0.017 mol) of 3-(4-aminobenzenesulfonyl)acrylonitrile are added, followed by 1.6 ml of pyridine. The reaction mixture is allowed to stand at room temperature for 24 hours. A yellowish solid is recovered by filtration and, after drying, is recrystallized from methyl ethyl ketone. There is thus recovered a yellow solid having a melting point of 210°–212°, believed to be N'-4-(2-cyanoethenesulfonyl)phenyl N''-3-(2-cyanoethenesulfonyl)-phenylsulfamoylbenzamide:

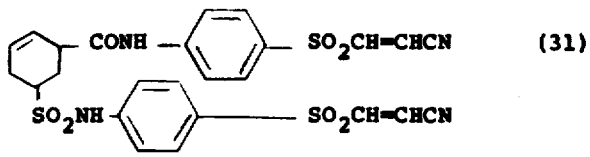

(31)

EXAMPLE 32:
3-[4-(4-DICHLOROCARBOSTYRENESUL- FONAMIDO)BENZENESULFONYL]ACRYLO- NITRILE 14.2 g (0.05 mol) of dichlorocarbostyrenesulfonyl chloride is dissolved in 25 ml dioxane and the resulting solution is added to a solution of 10.4 g (0.05 mol) of 3-(4-aminobenzenesulfonyl)acrylonitrile in 75 ml dioxane containing 4 ml pyridine. The reaction mixture is stirred at room temperature for 16 hours and then poured into 400 ml of water. A mixture of separated solid and finely dispersed solid results; the mixture is extracted with 400 ml of chloroform. The chloroform layer is thereafter washed with water, separated, dried over anhydrous magnesium sulfate, and evaporated, giving a brown semi-solid which is treated with ethanol to give 3-[4-(4-DICHLOROCARBOSTYRENESUL- FONAMIDO)BENZENESULFONYL]acrylonitrile:

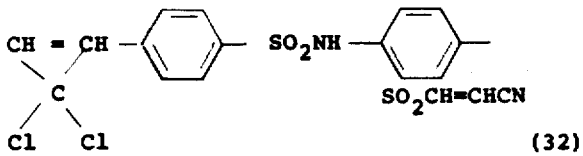

(32)

EXAMPLE 33:
N,N'-BIS-[4-(2-CYANOETHENESULFONYL)- PHENYL]-1,3-PHENYLENESULFONAMIDE 2.8 g (0.01 mol) m-benzene disulfonyl chloride are dissolved in 50 ml of dioxane; 4.2 g (0.02 mol) of 3-(4-aminobenzenesulfony)acrylonitrile are added thereto followed by 1.6 ml of pyridine. The reaction mixture is

EXAMPLE 34:
4,4'-N,N'-bis-[4-(2-CYANOETHENESULFONYL)- PHENYLSULFAMOYL]DIPHENYL ETHER Oxy-bis-benzene-4-sulfonyl chloride (0.02 mol) and 3-(4-aminobenzenesulfonyl)acrylonitrile (0.04 mol) are reacted in acetone solution in the presence of pyridine. The reaction is carried out at room temperature for 16 hours, after which the product is precipitated in water, extracted with chloroform and worked-up. There is thus obtained a yellow solid consisting of 4,4'-N,N'-bis[4-(2-cyanoethenesulfonyl)-phenylsulfamoyl]diphenyl ether:

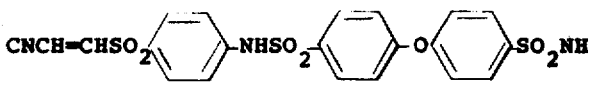

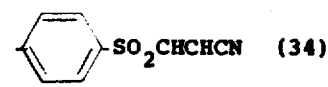

(34)

EXAMPLE 35:
3-[4-(2-NAPHTHALENESULFONAMIDO)BEN- ZENESULFONYL]ACRYLONITRILE 22.5 grams (0.1 mol) naphthalene-2-sulfonyl chloride are dissolved in 300 ml of chloroform and 21 g (0.1 mol) of 3-(4-aminobenzenesulfonyl)acrylonitrile are added, followed by 8 g of pyridine dissolved in 100 ml chloroform added portionwise. The reaction mixture is left at room temperature for 48 hours, filtered, and the filtrate is thereafter washed with water, 5% hydrochloric acid solution, 5% sodium bicarbonate solution in water, and water, in sequence. The chloroform layer is dried over anhydrous sodium sulfate and concentrated by distilling off the major part of the chloroform under vacuum. After cooling crystals form which are recrystallized from ethanol, giving a product having a melting point of 194°–196° C, consisting of 3-[4-(2-naphthalenesulfonamido)benzenesulfonyl]acrylonitrile:

(35)

EXAMPLE 36:
3-[3-(2-NAPHTHALENESULFONAMIDO)-4- METHYL BENZENESULFONYL]ACRYLONITRILE

The procedure of Example 12 is repeated, utilizing 22.7 g (0.1 mol) of naphthalene-2-sulfonyl chloride instead of benzenesulfonyl chloride. A quantitative yield of a yellow solid having a melting point of 214°–216° C is obtained 3-[3-(2-naphthalenesulfonamido)-4-methyl benzenesulfonyl]acrylonitrile:

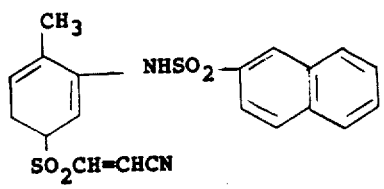

(36)

EXAMPLE 37: NAPHTHALENE-2,6-BIS-SULFON-[4-(2-CYANOETHENESULFONYL) ANILIDE]

Naphthalene-2,6-disulfonyl chloride (6.2 g, 0.02 mol) is dissolved in 100 ml dimethylformamide; to the solution is added, in 2–3 portions over about a minute, a solution of 3-(4-aminobenzenesulfonyl)acrylonitrile in 50 ml dimethylformamide containing 6 ml triethylamine (8.4 g, 0.04 mol). The temperature rises to 35° C by the exothermic reaction. The reaction mixture is maintained at room temperature for 2 hours and filtered to separate triethylamine hydrochloride therefrom. Addition of chloroform to the filtrate precipitates the product which, after washing with ethanol/water and drying, is in the form of a slightly off-white powder having a melting point of 312° C. The product is almost insoluble in ethanol, chloroform and acetone but is soluble in dimethylformamide and dimethylsulfoxide. It is naphthalene-2,6-bis-sulfon-[4-(2-cyanoethenesulfonyl)anilide]:

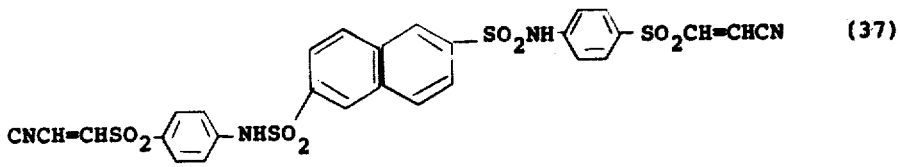

(37)

EXAMPLE 38: 3-[4-(2-ACETAMIDO-1,3,4-THIADIAZOLE-5-SULFONAMIDO)BENZENESULFONYL]ACRYLONITRILE 5.2 g (0.025 mol) of 3-(4-aminobenzenesulfonyl)acrylonitrile are dissolved in 100 ml acetone, and 4.5 ml (0.02 mol) triethylamine are added thereto. The resulting solution is added to 7 g (0.029 mol) of 2-acetamido-1,3,4-thiadiaza-5-sulfonyl chloride in 100 ml acetone, containing 100 ml dimethylformamide. The reaction mixture is maintained at room temperature for 70 hours. After addition of water a sticky brown material separates, which later solidifies and is recrystallized from acetic acid-water. This is 3-[4-(2-acetamido-1,3,4-thiadiazole-5-sulfonamido)benzenesulfonyl]acrylonitrile:

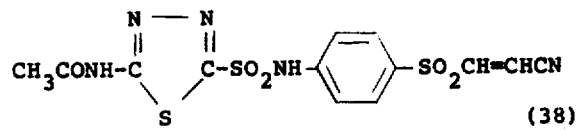

(38)

EXAMPLE 39: 2-CYANOVINYL 4-(3-FLUOROSULFONYLBENZENESULFONAMIDO)PHENYL SULFONE

To an acetone solution of 10.4 g (0.05 mol) 2-cyanovinyl 4-aminophenyl sulfone is added 12.8 g (0.05 mol of 3-fluorosulfonylbenzenesulfonyl chloride at room temperature, with agitation. The sulfonyl chloride dissolves immediately, giving a clear yellow solution. To this mixture is added over a ten minute period an acetone solution of 1,4-diazabicyclo[2.2.2]-octane (11.2 g, 0.05 mol). A light yellow precipitate forms almost at once; the reaction mixture is maintained at about 25° C for 30 minutes with stirring. Precipitation in water and workup affords a bright yellow powder, 2-cyanovinyl 4-(3-fluorosulfonylbenzenesulfonamido)-phenyl sulfone:

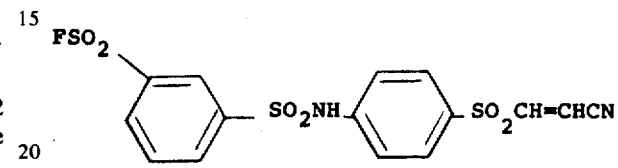

EXAMPLE 40: 3-[4-(4-METHYLBENZENESULFINAMIDO)BENZENESULFONYL]ACRYLONITRILE 17.5 g p-toluenesulfinyl chloride (obtained by treating sodium toluenesulfinate.2H$_2$O with thionyl chloride) is dissolved in 100 ml of acetone and this solution is added at room temperature and with stirring to a solution of 20.8 g (0.1 mol) of 2-cyanovinyl 4-aminophenyl sulfone in 250 ml of acetone. Shortly thereafter a solution of 11.2 g (0.1 mol) of 1,4-diazabicyclo[2.2.2]octane in 150 ml of acetone is added over about 10 minutes and the reaction mixture is stirred for another 20 minutes. The reaction mixture is filtered, evaporated in air to about a third of its volume, and then poured into cold water. The precipitate is filtered, washed and dried to give 3-[4-(4-methylbenzenesulfinamido)benzenesulfonyl]acrylonitrile:

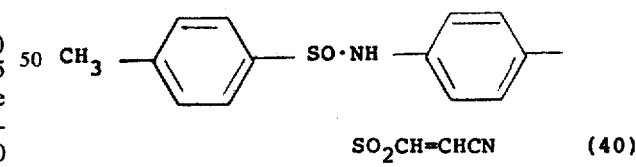

(40)

EXAMPLE 41: 3-(4-BENZENESULFINAMIDOBENZENESULFONYL)ACRYLONITRILE

A solution of 5.1 g (0.02 mol) of 2-cyanovinyl 4-sulfinimidophenyl sulfone (Example 44) in 50 ml of dioxane is slowly and dropwise added to a solution of 4.1 g (0.025 mol) of a phenylmagnesium bromide solution in ether at 0°–5° C and stirred for onehalf hour. The reaction mixture is filtered and then carefully heated to about 40° C for one hour. After cooling, the reaction mixture is poured into a well-stirred 5% hydrochloric acid solution containing ice. When the hydrolysis is completed, the precipitate is filtered and washed acid-free, and dried at 40° C under vacuum. 3-(4-benzenesulfinamidobenzenesulfonyl)acrylonitrile is obtained, having the formula:

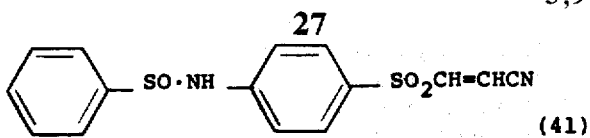

(41)

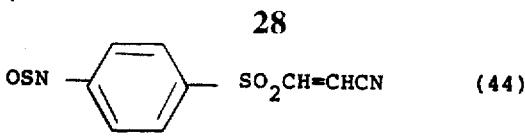

(44)

EXAMPLE 42: 3-(4-TRICHLOROSULFENAMIDOBENZENESULFONYL)ACRYLONITRILE

To a solution of 20.8 g (0.1 mol) of 2-cyanovinyl 4-aminophenyl sulfone and 12.2 g (0.1 mol) of dimethylaniline in 250 ml of dichloromethane there is added a solution of 22.3 g (0.12 mol) trichloromethanesulfenyl chloride in 25 ml dichloromethane, with cooling and occasional stirring. The reaction mixture is allowed to stand at room temperature for 48 hours. A yellowish solid is obtained which is filtered off and left to dry in air whereby it turns pink-red. The product is washed with 5% HCl solution, 10% sodium bicarbonate solution and water, and the separated hydrocarbon layer then dried over anhydrous sodium sulfate. After addition of petroleum ether and cooling a yellow solid separates, which is dried and melted at 180°–185° C, constituting 3-(4-trichlorosulfenamidobenzenesulfonyl)acrylonitrile:

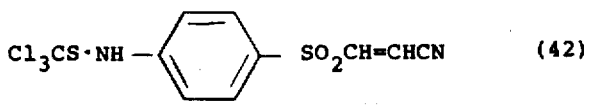

(42)

EXAMPLE 43: 3-[4-(4-NITROBENZENESULFENAMIDO)BENZENESULFONYL]ACRYLONITRILE 10.4 g (0.05 mol) 2-cyanovinyl 4-aminophenyl sulfone is dissolved in 75 ml of dioxane, and 9.5 g (0.05 mol) of p-nitrobenzenesulfenyl chloride dissolved in 60 ml of dioxane is added simultaneously with 18 ml of 2N NaoH. The solutions are added portionwise and with stirring. After about 15 minutes, the reaction mixture is poured into 300 ml of chloroform. The resulting dispersion is washed with 1N sulfuric acid, and then several times with water. The chloroform layer is dried over anhydrous magnesium sulfate, filtered and evaporated, giving a yellowish brown semi-solid consisting largely of 3-[4-(4-nitrobenzenesulfenamido)benzenesulfonyl]acrylonitrile:

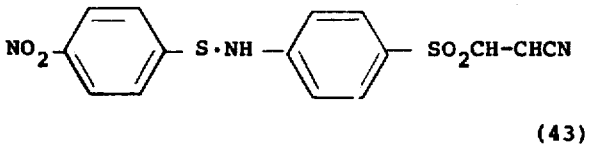

(43)

EXAMPLE 44: 3-(4-SULFINYLIMIDOBENZENESULFONYL)ACRYLONITRILE 10.4 g (0.05 mol) of 2-cyanovinyl 4-aminophenyl sulfone is dispersed in 100 ml of benzene, and 8 ml of thionyl chloride in 25 ml of benzene is added thereto. The reaction mixture is heated to 60° C in an oil bath whereby a fairly brisk evolution of gas (HCl) takes place. The reaction mixture is then boiled at reflux for four hours, filtered and evaporated to dryness. A yellowish-white solid is obtained, 3-(4-sulfinylimidobenzenesulfonyl)acrylonitrile:

EXAMPLE 45: TRIS-N,N',N''-4-(2-CYANOETHENESULFONYL)PHENYL PHOSPHORAMIDE

To an acetone solution of 124.8 g (0.6 mol) of 2-cyanovinyl 4-aminophenyl sulfone is added 15.3 g (0.1 mol) of phosphoryl chloride dropwise, with stirring, at about 10° C. After the addition is completed the reaction mixture is stirred for one hour and then a solution of 34 g (0.3 mol) 1,4-diazabicyclo[2.2.2]octane in 500 ml of acetone is added. The yellow slurry formed is stirred for another four hours at about room temperature and then filtered to separate amine hydrochlorides. The filtrate is poured into cold water and the yellowish coarse precipitate is recovered by filtration and successively washed with dilute hydrochloric acid and hot water, and dried at 50° C in a vacuum oven to give the tris-phosphoramide.

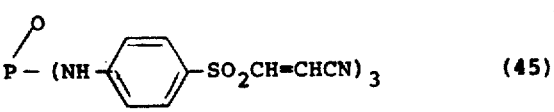

(45)

EXAMPLE 46: CHLORO-DI-[3-(2-CYANOETHENESULFONYL)-5-METHYLANILIDO]PHOSPHINE OXIDE 15.3 g phosphoryl chloride (0.1 mol) in 100 ml acetone is slowly added to a stirred acetone solution of 88.8 g (0.4 mol) of 2-cyanovinyl 4-methyl-3-aminophenyl sulfone maintained at 0–5° C. The reaction mixture is stirred overnight at about room temperature and is then filtered and worked up as in Example 45, giving the above product (which may also be termed bis[3-(2-cyanoethenesulfinyl)-5-methylphenylamido]phoshorochloridate):

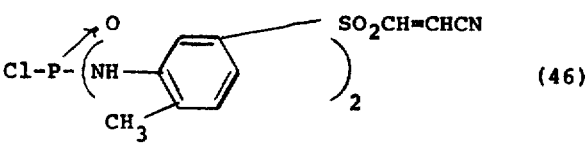

(46)

EXAMPLE 47: OCTYL 3-(4-DICHLOROPHOSPHORAMIDOBENZENESULFONYL) ACRYLATE 34 g (0.1 mol) of 2-octylcarbonylvinyl 4-aminophenyl sulfone is dispersed in 16 g of phosphoryl chloride; a small amount of dimethylformamide is added from time to time to keep the mixture fluid and it is slowly heated to reflux with stirring for two hours. The cooled reaction mixture is treated with ether to remove solvent and impurities and leave octyl 3-(4-dichlorophosphoramidobenzenesulfonyl)acrylate:

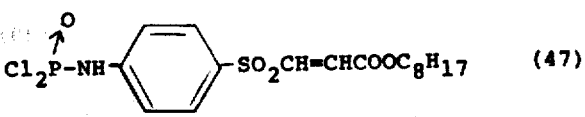

(47)

EXAMPLE 48: FLUORO-DI-(4-METHYL 3-(2-CYANOETHENESULFONYLANILIDO)PHOSPHINE OXIDE

Chloro-di[3-(2-cyanoethenesulfonyl)-5-methylanilido]phosphine oxide prepared as in Example 46 (5.3 g or 0.01 mol) is dissolved in 50 ml of dimethylformamide and 1.2 g potassium fluoride (0.02 mol) is added thereto. The mixture is heated with stirring and maintained at 80° C for six hours. After cooling the reaction mixture is dispersed in water and the solid precipitate filtered off and recrystallized from ethanol, giving fluoro-di-(4-methyl-3-(2-cyanoethenesulfonylanilido)phosphine oxide

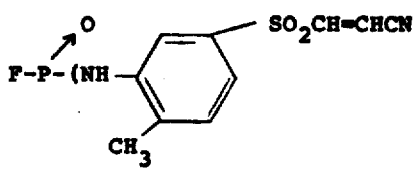

(48)

Preparation of the indicated compound should only be conducted by those experienced in preparing highly toxic fluorine-containing phosphorus compounds, employing the standard precautions utilized in such instances. Thus, the preparation may be carried out in dry boxes or under a hood, and oxygen and atropine or like materials should be available in case of emergency. Similarly, glassware or other experimental equipment should be detoxified.

EXAMPLE 49: TRIS-4-(2-CYANOETHENESULFONYLANILIDO)-PHOSPHINE SULFIDE

The named compound:

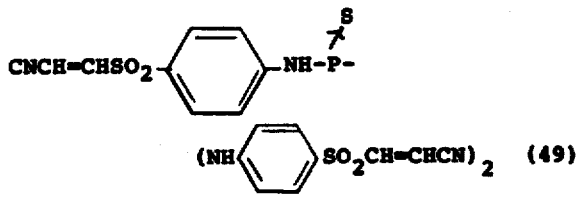

(49)

is prepared by a procedure similar to the one described in Example 45 but using thiophosphoryl chloride instead of phosphoryl chloride. In similar fashion numerous other thiophosphoramides can be made.

EXAMPLE 50: 4-DI-HEPTYLAMIDOPHOSPHORAMIDONAPHTHYL 2-CYANOVINYL SULFONE 2-cyanovinyl 4-aminoaphthyl sulfone (19 grams, 0.05 mol) is dispersed in 200 ml of tetrachloromethane; 11 grams of PCl$_5$ are added thereto. The reaction mixture is boiled at reflux until the evolution of HCl ceases. Volatile materials are removed by evaporation under vacuum and the remaining solid is washed with petroleum ether and dried. It consists mainly of 4-(2-cyanoethenesulfonyl)anilidophosphorus trichloride with smaller amounts of intermediate tetrachloride.

The reaction product is dissolved in 100 ml of dioxane, briefly heated to boiling and cooled. To the cooled solution is added dropwise 0.1 mol (4.6 g) of anhydrous formic acid. After the evolution of carbon monoxide and hydrogen chloride is completed the reaction mixture is filtered, and poured into ice water. The solid hydrolyzate is recovered by filtration, washed with water and dried, and consists of 4-dichlorophosphoramidonaphthyl 2-cyanovinyl sulfone.

The product is dissolved in 100 ml of acetone, and a mixture of 0.2 mol of heptylamine and 0.2 mol of triethylamine per mole of intermediate, diluted with a little acetone, is added to the stirred solution at 20°–30° C. After two hours, the reaction mixture is filtered and poured into water and the precipitate is recovered by filtration and drying, giving 4-di-heptylamidophosphoramidonaphthyl 2-cyanovinyl sulfone:

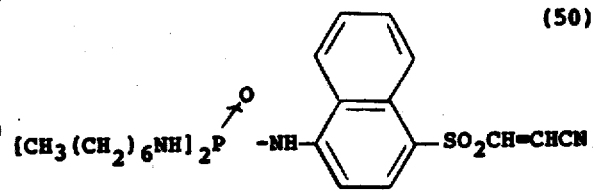

(50)

EXAMPLE 51: BIS-DIMETHYLAMIDO-4-(2-CYANOETHENESULFONYL)ANILIDOPHOSPHINE OXIDE

Bis-dimethylamino-chlorophosphine oxide, prepared from dimethylamine and phosphoryl chloride according to B.C. Saunders et al as described in the Journal of the Chemical Society 1949,2921, is dissolved in acetone (34.2 g or 0.2 mol in 300 ml acetone) and added gradually at room temperature to a solution of 0.2 mol (41.6 g) of 2-cyanovinyl 4-aminophenyl sulfone in 300 ml of acetone. A solution of 22.4 g (0.2 mol) of 1,4-diazabicyclo[2.2.2]octane is added with stirring and the reaction mixture is stirred for about 30 minutes. The amine hydrochlorides are filtered off and the solid reaction product is recovered by evaporation of the solvent: bis-dimethylamido-4-(2-cyanoethenesulfonyl)anilidophosphine oxide:

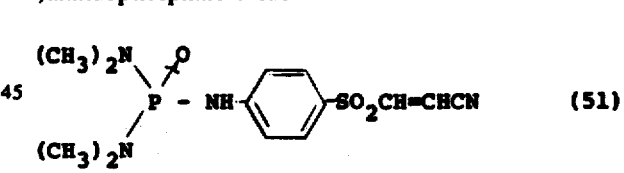

(51)

EXAMPLE 52: BIS-(2-CHLOROETHYL)AMIDO-DI-4-(2-CYANOETHENESULFONYLANILIDO)PHOSPHINE OXIDE

Di-(2-chloroethyl)amidophosphorodichloridate is prepared according to H. Brintzinger et al in Chemische Berichte 82, 389–99 (1949) from bis-(2-chloroethyl)amine hydrochloride and phosphoryl chloride in the presence of pyridine. 0.03 mol (7.8 g) of this material is dissolved in 100 ml of acetone and added to an acetone solution of 0.03 mole (6.3 g) of 2-cyanovinyl 4-aminophenyl sulfone. To the stirred mixture is added in 2–3 portions a 10% solution of 1,4-diazabicyclo[2.2.2.]octane in acetone. After a few minutes a yellow slurry forms which is stirred at room temperature for 30 minutes. After filtration to remove the amine hydrochlorides the filtrate is reduced to about half its volume by evaporation and then mixed with chloroform, washed with water and worked up. The light yellow solid is di-(2-chloroethyl)amido-di-4-(2-cyanoethenesulfonylanilido)phosphine oxide:

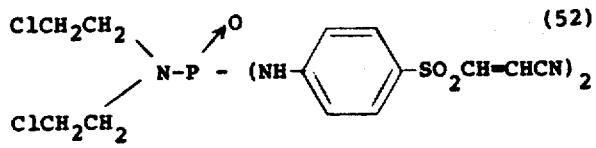

EXAMPLE 53:
4-(DIHYDROXYPHOSPHORAMIDOPHENYL) 2-CARBAMOYLVINYL SULFONE 3.5 grams (0.01 mol) of 4-dichlorophosphoramidophenyl 2-carbamoylvinyl sulfone (see Example 61 below) is dispersed in boiling benzene, and 0.02 mole of anhydrous formic acid is added thereto. The reaction mixture is boiled for two hours whereby to hydrolyze the dichloride, with the evolution of carbon monoxide and hydrogen chloride, to the monophosphoramide 4-(dihydroxyphosphoramidophenyl) 2-carbamoylvinyl sulfone:

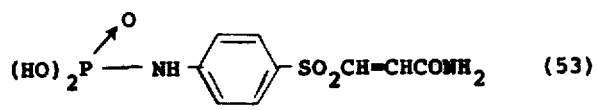

EXAMPLE 54:
4-DIETHOXYPHOSPHORAMIDOPHENYL 2-CYANOVINYL SULFONE 2-trifluoromethylvinyl 4-aminophenyl sulfone is prepared by the addition of 4-acetamidobenzenesulfonyl iodide to 1,1,1-trifluoropropene followed by dehydrohalogenation and removal of the N-acetyl protective group by hydrolysis in a hydrochloric acid-ethanol mixture. The product is dissolved in acetone (25.1 g or 0.1 mol), an acetone solution of 0.1 mol (17.3 g) of ethylphosphorochloridate in acetone added, followed by 11.2 g of 1,4-diazabicyclo[2.2.2]octane in 10% acetone solution. The reaction mixture is stirred for one hour at room temperature, filtered, most of the acetone evaporated, and the residue is mixed with chloroform, washed and worked up. There is thus obtained 4-diethoxyphosphoramidophenyl 2-trifluoromethylvinyl sulfone:

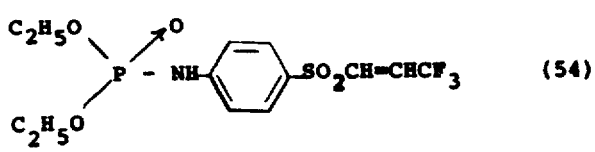

EXAMPLE 55:
4-DIMETHOXYPHOSPHORAMIDOPHENYL 2-NITROVINYL SULFONE 11.4 g (0.05 mol) of 2-nitrovinyl 4-aminophenyl sulfone is obtained by reacting 1-chloro-2-nitroethane with sodium 4-acetamidobenzenesulfinate, followed by acid hydrolysis to remove the N-acetyl group. This product is dissolved in acetone, and to the resulting solution an acetone solution of 0.05 mol (7.3 g) of methyl phosphorochloridate is added, followed by a 10% acetone solution of 1,4-diazabicyclo[2.2.2]-octane. The reaction mixture is stirred for about 45 minutes, filtered from amine hydrochlorides, evaporated, taken up in chloroform and worked up. The resulting product, which may also be termed 0,0-bis-methyl-N-4-(2-cyanoethenesulfonyl)phenyl phosphoramide, has the formula:

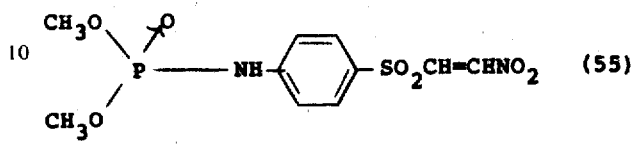

EXAMPLE 56:
BIS-(2,3-DIBROMOPROPOXY)-[4-(2-CYANOETHENESULFONYL)ANILIDO]PHOSPHINE OXIDE

To a solution of 0.1 mol (20.8 g) 2-cyanovinyl 4-aminophenyl sulfone in 200 ml acetone is added 52 grams (0.1 mol) of 2,3-dibromopropyl phosphorochloridate (White Chemical Corporation, Bayonne, New Jersey) with stirring. A clear solution results. To this is added portionwise 11.2 grams of 1,4-diazabicyclo[2.2.2] octane, which dissolves rapidly therein. A yellow precipitate forms and the reaction mixture is stirred for 30 minutes at room temperature. About 20 ml of water is added, the amine hydrochlorides going into solution. The solution is poured into about one liter of water, and the precipitate is collected by filtration and air dried. It is then extracted with ether several times to remove unreacted material. The resulting yellow powder has a rather strong odor and consists of the above-named product, which may also be termed 0,0-bis(2,3-dibromopropyl)-N-4-(2-cyanoethenesulfonyl)-phenyl phosphoramide:

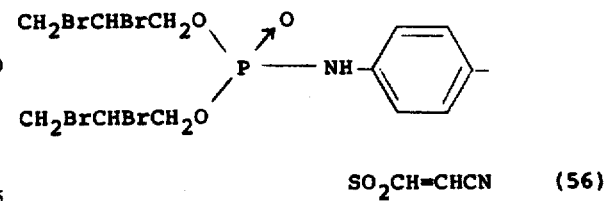

EXAMPLE 57:
DI-4-(2-CYANOETHENESULFONYL)ANILIDO-PHOSPHINE OXIDE 10.4 g (0.05 mol) of 2-cyanovinyl 4-aminophenyl sulfone is dissolved in 100 ml of acetone and the solution cooled to 0° C. 1.4 grams (0.1 mol) of phosphorus trichloride dissolved in 20 ml of acetone is added dropwise with stirring. After about 40 minutes the reaction mixture is poured into ice water with vigorous stirring. The intermediate initially formed hydrolyzes easily upon the addition of water to form di-4-(2-cyanoethenesulfonyl)anilidophosphine oxide, which can be recovered by filtration and drying at low temperature under vacuum. The product appears to be somewhat unstable.

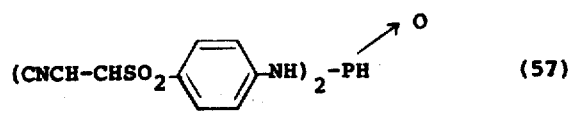

EXAMPLE 58: PHENYL-DI-[4-(2-CYANOETHENESULFONYL)ANILIDO]PHOSPHINE OXIDE

To a filtered solution in acetone of 20.8 grams 2-cyanovinyl 4-aminophenyl sulfone is added 0.05 mol (10 g) of dichlorophenyl phosphine oxide. A mixture of 20 ml tributylamine in an equal amount of acetone is added and the solution is stirred for an hour at room temperature. Chloroform is added and the mixture is washed with water. Evaporation of the dried chloroform layer yields a soft yellowish solid consisting largely of phenyl-di-[4-(2-cyanoethenesulfonyl)anilido]phosphine oxide:

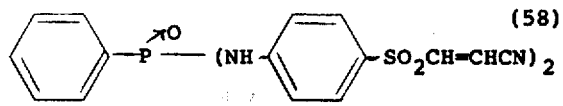

(58)

EXAMPLE 59: PHENYL-DI-[4-(2-CYANOETHENESULFONYL)ANILIDO]PHOSPHINE SULFIDE

The same procedure is utilized as in Example 58 reacting, however, dichlorophenyl phosphine sulfide in the same molecular proportions. A soft red-brown solid is produced constituting crude phenyl-di-[4-(2-cyanoethenesulfonyl)anilido]phosphine chloride:

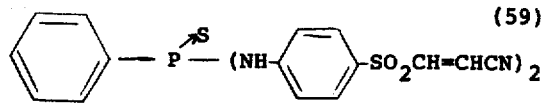

(59)

EXAMPLE 60: DI-AZIRIDINO-4-(2-OCTYLCARBONYLETHENESULFONYL)ANILIDOPHOSPHINE OXIDE

To a solution of 22 g (0.05 mol) of octyl 3-[(4-dichlorophosphoramido)benzenesulfonyl]acrylate in acetone is added a mixture of 4.3 g aziridine and 15 ml of triethylamine in 50 ml of acetone at room temperature, and the reaction mixture is stirred for two hours. After filtration the acetone solution is poured into cold water and the precipitate is collected and dried, affording di-aziridino-4-(2-octylcarbonylethenesulfonyl)anilidophosphine oxide:

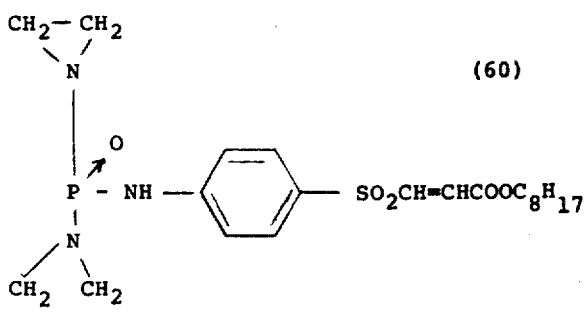

(60)

EXAMPLE 61: DI-MORPHOLINO-4-(2-CARBAMOYLETHENESULFONYLANILIDO)PHOSPHINE OXIDE 6.9 g (0.02 mol) 4-dichlorophosphoramidophenyl 2-carbamoylvinyl sulfone is prepared from phosphoryl chloride and 2-carbamoylvinyl 4-aminophenyl sulfone. To a solution of this compound in acetone a mixture of 3.6 g (0.04 mol) morpholine and 6 ml tri-ethylamine dissolved in 25 ml of acetone is added. The reaction mixture is stirred for two hours at approximately 20° C, filtered and the filtrate is poured into ice water. From the precipitate is obtained di-morpholino-4-(2-carbamoylethenesulfonylanilido)phosphine oxide:

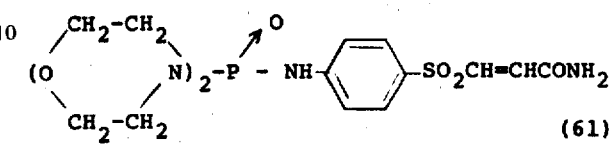

(61)

ANTIMICROBIAL TESTING

The structures of the several compounds of the preceding examples are tabulated in Tables I–III below, together with the antimicrobial activities of compounds selected therefrom.

In the test program, the minimum inhibitory concentrations of the respective test compounds against various Gram positive and Gram negative bacteria were determined, employing the "button assay" method. The test organisms utilized were standard cultures of *Staphylococcus aureus* ATCC 6538 DR, a penicillin resistant Gram positive bacterium; *Bacillus subtilis* ATCC 9525, a spore-forming Gram positive bacillus; and *Salmonella typhosa* ATCC 6539, a Gram negative bacterium.

In the tests the respective compounds were dissolved in a suitable solvent, usually acetone or dimethylsulfoxide, to give solutions with known concentrations of active material. The highest concentration was ordinarily 1000 ppm (parts per million) [0.1%], and dilutions were made in suitable steps down to 1 ppm. Penicillin test buttons of filter paper having a diameter of 13 mm (socalled "Peniassay" buttons) were added to each solution within a test tube and left submerged for five minutes. They were then removed and left to dry on paper towels under sterile conditions. A laminar flow sterile cabinet equipped with ultraviolet lamps operating under positive air pressure was utilized for this purpose.

An 18–24 hour old nutrient broth culture (standard 1.5% nutrient agar) prepared in conventional manner from a slant and having passed through at least three consecutive daily transfers was used for inoculation. Melted and cooled sterile agar (45° C) was inoculated with the respective broth cultures by addition of 20 ml broth per liter of agar. The agar was then dispensed into Petri dishes (20 ml per plate) under sterile conditions and allowed to harden.

The test buttons were placed on the surface of the hardened agar and the plates incubated for 24 hours at 37° C. Where, on inspection, a clear zone of inhibition appeared around the button, inhibition of growth was presumed. Where growth touched the button there was no inhibition. For each of the test compounds, the lowest concentration showing a clear zone is reported as the inhibitory concentration in the following table.

The anti-fungal activity of the test compounds was determined employing the "agar incorporation" technique, utilizing spores from *Aspergillus niger* ATCC 6257 as a representative organism. Test solutions were prepared as described above in acetone or dimethylsulfoxide. A source of carbon agar such as Mycophil Agar was used. The agar was melted and cooled and placed in a constant temperature water bath at 45°C + 3°C. About 13–14 ml of the agar was then poured into a sterile Petri dish, the required amount of test solution to give the desired concentration immediately added thereto, and the dish rotated and swirled by hand to obtain a uniform mixture before the agar hardened.

The hardened plates were inoculated with the test organism by fishing spores from a 7–14 day old slant with the inocculating needle and spotting the spores on the plates, usually in several places. The inoculated plates were incubated for four days in an incubator maintained at 28°C +2°C and with a relative humidity of 95%+.

The lowest concentration of each test compound showing no growth or sporulation of the test organism was taken as the minimum inhibitory concentration and is reported in the following tabulation.

The button assay and agar incorporation tests were also utilized to determine the corresponding inhibitory concentrations of various control materials, viz., the following well known commercial antimicrobials and fungicides: hexachlorophene, tribromosalicylanilide, trichlorocarbanilide, Captan (N-(trichloromethylthio)4cyclohexene-1,2-dicarboximide) and Zineb (zinc ethylenebis[dithiocarbamate]). The minimum inhibitory concentration of each of the various control materials against the respective organisms is indicated in Table IV below:

TABLE I

STRUCTURE AND ANTIMICROBIAL ACTIVITY OF TEST COMPOUNDS $R'(SO_2NH-Ar-SO_2CH=CH-X)_m$

| Example | R' | Ar | X | m | Antifungal Activity A. niger[1] | Antibacterial Activity B.subtilis[2] | S. aureus[2] | S. typhosa[2] |
|---|---|---|---|---|---|---|---|---|
| 1 | $CH_3$ |  | CN | 1 | >1,000 | 100 | 300 | 1,000 |
| 2 | $C_2H_5$ | " | CN | 1 | >1,000 | 20 | 100 | 20 |
| 3 | $C_4H_9$ | " | CN | 1 | >1,000 | 20 | 50 | 50 |
| 4 | $C_{16}H_{33}$ | " | CN | 1 | 500 | 20 | 20 | 50 |
| 5 | $CF_3$ | " | CN | 1 | — | — | — | — |
| 6 | $CF_3$ |  | CN | 1 | — | — | — | — |
| 7 | $HCF_2$ |  | CN | 1 | — | — | — | — |
| 8 | $C_8F_{17}$ |  | $COOC_2H_5$ | 1 | — | — | — | — |
| 9 | $CH_2=CH$ |  | CN | 1 | 100 | 10 | 20 | 50 |
| 10 |  | " | CN | 1 | >1,000 | 5 | 5 | 5 |
| 11 | 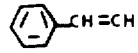 | " | CN | 1 | >1,000 | 50 | 20 | 50 |
| 12 | " |  | CN | 1 | >1,000 | 100 | 100 | 100 |
| 13 | 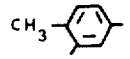 |  | CN | 1 | >1,000 | 5 | 5 | 5 |
| 14 |  |  | $CONH_2$ | 1 | — | — | — | — |
| 15 | " | " | $COOC_2H_5$ | 1 | — | — | — | — |
| 16 |  | " | CN | 1 | >1,000 | 20 | 20 | 20 |
| 17 |  | " | CN | 1 | 300 | 10 | 5 | 10 |

TABLE I-continued
STRUCTURE AND ANTIMICROBIAL ACTIVITY OF TEST COMPOUNDS
R′(SO$_2$NH—Ar—SO$_2$CH=CH—X)$_m$
| Example | R′ | Ar | X | m | Antifungal Activity A. niger[1] | Antibacterial Activity B.subtilis[2] | S. aureus[2] | S. typhosa[2] |
|---|---|---|---|---|---|---|---|---|
| 18 | 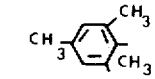 |  | CN | 1 | 100 | 10 | 5 | 10 |
| 19 | 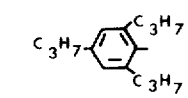 | ″ | CN | 1 | >1,000 | 1,000 | 1,000 | 1,000 |
| 20 | 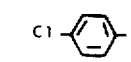 | ″ | CN | 1 | >1,000 | 5 | 20 | 10 |
| 21 | 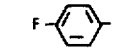 | ″ | CN | 1 | — | — | — | — |
| 22.1 | 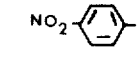 | ″ | CN | 1 | >1,000 | 50 | 100 | 50 |
| 22.2 | 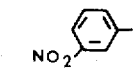 | ″ | CN | 1 | — | — | — | — |
| 22.3 | 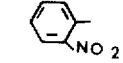 | ″ | CN | 1 | >1,000 | tr. 50[3] | 10 | 100 |
| 23.1 | 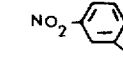 | ″ | CN | 1 | 100 | 50 | 5 | 50 |
| 23.2 | 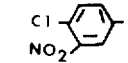 | ″ | CN | 1 | 1,000 | 300 | 100 | 100 |
| 23.3 | 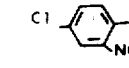 | ″ | CN | 1 | 100 | 10 | 10 | 20 |
| 24 | 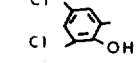 | ″ | CN | 1 | 1,000 | 300 | 300 | 300 |
| 25 | 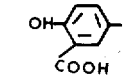 | ″ | CN | 1 | 500 | 50 | 50 | 50 |
| 26 |  | ″ | CN | 1 | >1,000 | 10 | 10 | 10 |
| 27 | 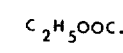 | ″ | CN | 1 | 100 | 20 | 10 | 10 |
| 28 | 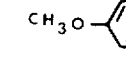 | ″ | CN | 1 | >1,000 | 10 | 1 | 5 |
| 29.1 | 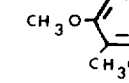 | ″ | CN | 1 | 300 | 10 | 20 | 10 |

TABLE I-continued

STRUCTURE AND ANTIMICROBIAL ACTIVITY OF TEST COMPOUNDS $R'(SO_2NH—Ar—SO_2CH=CH—X)_m$

| Example | R' | Ar | X | m | Antifungal Activity A. niger[1] | Antibacterial Activity B.subtilis[2] | S. aureus[2] | S. typhosa[2] |
|---|---|---|---|---|---|---|---|---|
| 29.2 | $CH_3O$—phenyl— | —phenyl— | CN | 1 | 1,000 | 20 | 20 | 50 |
| 30 | $CH_3CONH$—phenyl— | " | CN | 1 | >1,000 | 50 | 50 | 50 |
| 31 | phenyl-CONH—phenyl—$SO_2CH=CHCN$ | " | CN | 1 | 100 | 20 | 20 | 20 |
| 32 | CH=CH—phenyl— with $CCl_2$ | " | CN | 1 | 1,000 | 5 | 5 | 5 |
| 33 | phenyl— | " | CN | 2 | >1,000 | 10,000 | 300 | 100 |
| 34 | phenyl-O-phenyl— | " | CN | 2 | >1,000 | 100 | 100 | 50 |
| 35 | naphthyl— | " | CN | 1 | >1,000 | 5 | 10 | 5 |
| 36 | " | $H_3C$—phenyl— | CN | 1 | — | — | — | — |
| 37 | naphthyl— | —phenyl— | CN | 2 | 1,000 | 50 | 20 | 20 |
| 38 | $CH_3CONH$—thiadiazolyl— | " | CN | 1 | 1,000 | 50 | 500 | 100 |
| 39 | $FSO_2$—phenyl— | " | CN | 1 | — | — | — | — |

[1]Minimum inhibitory concentration of the test compound in parts per million (ppm) to inhibit growth or sporulation of the test organism in the agar incorporation test.

[2]Minimum inhibitory concentration of the test compound in parts per million (ppm) showing a clear zone of inhibition in the button assay test.

[3]At this concentration only a trace of growth of the organism was noted.

TABLE II

STRUCTURE AND ANTIMICROBIAL ACTIVITY OF TEST COMPOUNDS $R'[S(O)_pNH—Ar-SO_2CH=CHX]_m$

| Example | R' | p | Ar | X | m | Antifungal Activity A. niger[1] | Antibacterial Activity B.subtilis[2] | S.aureus[2] | S.typhosa[2] |
|---|---|---|---|---|---|---|---|---|---|
| 40 | $CH_3$—phenyl— | 1 | —phenyl— | CN | 1 | — | — | — | — |
| 41 | phenyl— | 1 | " | CN | 1 | — | — | — | — |
| 42 | $Cl_3$—C— | 0 | " | CN | 1 | +1,000 | 20 | 20 | 20 |
| 43 | $NO_2$—phenyl— | 0 | " | CN | 1 | 300 | 5 | 5 | 10 |

TABLE II-continued

STRUCTURE AND ANTIMICROBIAL ACTIVITY OF TEST COMPOUNDS

R'[S(O)$_p$NH—Ar-SO$_2$CH=CHX]$_m$

| Example | R' | p | Ar | X | m | Antifungal Activity A. niger[1] | Antibacterial Activity B.subtilis[2] | S.aureus[2] | S.typhosa[2] |
|---|---|---|---|---|---|---|---|---|---|
| 44 |  O=S=N-Ar-SO$_2$CH=CHX | | | CN | | 300 | 10 | 20 | 10 |

[1]Minimum inhibitory concentration of the test compound in parts per million (ppm) to inhibit growth or sporulation of the test organism in the agar incorporation test.
[2]Minimum inhibitory concentration of the test compound in parts per million (ppm) showing a clear zone of inhibition in the button assay test.

TABLE III

STRUCTURE AND ANTIMICROBIAL ACTIVITY OF TEST COMPOUNDS
(R")$_n$—Z—[NH—Ar—SO$_2$CH=CHX]$_q$

| Example | R" | n | Z | Ar | X | q | Antifungal Activity S.niger[1] | Antibacterial Activity B.subtilis[2] | S.aureus[2] | S.typhosa[2] |
|---|---|---|---|---|---|---|---|---|---|---|
| 45 | CNCH=CH-SO$_2$-C$_6$H$_4$-NH— | 1 | P=O | C$_6$H$_4$ | —CN | 2 | 300 | 5 | 50 | 50 |
| 46 | Cl— | " | " | 2,4-(CH$_3$)C$_6$H$_3$ | " | 2 | — | — | — | — |
| 47 | Cl— | 2 | " | C$_6$H$_4$ | —COOC$_8$H$_{17}$ | 1 | — | — | — | — |
| 48 | F— | 1 | " | 2,4-(CH$_3$)C$_6$H$_3$ | " | 2 | — | — | — | — |
| 49 | CNCH=CH-SO$_2$-C$_6$H$_4$-NH— | " | P=S | C$_6$H$_4$ | —CN | 2 | — | — | — | — |
| 50 | CH$_3$(CH$_2$)$_6$NH— | 2 | P=O | naphthyl | " | 1 | — | — | — | — |
| 51 | (CH$_3$)$_2$N— | " | " | C$_6$H$_4$ | " | 1 | 100 | 20 | 20 | 10 |
| 52 | (ClCH$_2$CH$_2$)$_2$N— | 1 | " | " | " | 2 | 100 | 10 | 10 | 10 |
| 53 | OH— | 2 | P=O | C$_6$H$_4$ | —CONH$_2$ | 1 | — | — | — | — |
| 54 | C$_2$H$_5$O— | 2 | " | " | —CF$_3$ | 1 | — | — | — | — |
| 55 | CH$_3$O— | " | " | " | —NO$_2$ | 1 | — | — | — | — |
| 56 | CH$_2$BrCHBrCH$_2$O— | " | " | " | —CN | " | 100 | 10 | 10 | 10 |
| 57 | H— | 1 | " | " | " | 2 | 100 | 20 | 20 | 20 |
| 58 | C$_6$H$_5$— | 1 | " | " | " | " | 100 | 10 | 20 | 10 |
| 59 | " | " | P=S, =O | " | " | " | 500 | 50 | 50 | 50 |
| 60 | aziridinyl (CH$_2$CH$_2$N—) | 2 | P=O | " | —COOC$_8$H$_{17}$ | 1 | — | — | — | — |

TABLE III-continued

STRUCTURE AND ANTIMICROBIAL ACTIVITY OF TEST COMPOUNDS
$(R'')_n-Z\text{-}[NH-Ar-SO_2CH=CHX]_q$

| Example | R'' | n | Z | Ar | X | q | Antifungal Activity S.niger[1] | Antibacterial Activity B.subtilis[2] | S.aureus[2] | S.typhosa[2] |
|---|---|---|---|---|---|---|---|---|---|---|
| 61 | 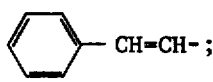 | 2 | '' | '' | —CONH$_2$ | 1 | — | — | — | — |

[1]Minimum inhibitory concentration of the test compound in parts per million (ppm) to inhibit growth or sporulation of the test organism in the agar incorporation test.

[2]Minimum inhibitory concentration of the test compound in parts per million (ppm) showing a clear zone of inhibition in the button assay test.

TABLE IV

ANTIMICROBIAL ACTIVITY OF CONTROL COMPOUNDS

| Controls | Antifungal Activity A.niger[1] | Antibacterial Activity B.subtilis[2] | S.aureus[2] | S.typhosa[2] |
|---|---|---|---|---|
| 3-(4-aminobenzenesulfonyl)acrylonitrile | 300 | 20 | 20 | 20 |
| 3-(4-acetamidobenzenesulfonyl)acrylonitrile | >1,000 | 20 | 50 | 20 |
| hexachlorophene | >1,000 | 5 | 5 | 20 |
| tribromosalicylanilide | >1,000 | 100 | 100 | 50 |
| trichlorocarbanilide | 1,000 | >10,000 | 10 | 10,000 |
| Captan | 300 | 100 | 25 | 25 |
| Zineb | >1,000 | 300 | 300 | >10,000 |

[1]Minimum inhibitory concentration of the test compound in parts per million (ppm) to inhibit growth or sporulation of the test organism in the agar incorporation test.
[2]Minimum inhibitory concentration of the test compound in parts per million (ppm) showing a clear zone of inhibition in the button assay test.

The acylamides of the present invention find other applications in addition to their use for controlling the growth of animal and plant organisms. Thus, they are strong absorbers of ultraviolet light and are thereby useful for protection against the undesirable effects of ultraviolet radiation, e.g., in cosmetic preparations against sunburn, and in plastics, textiles and the like in which they act as bi-functional protectants. Additionally, the phosphorus-containing acylamides hereof, and particularly those wherein R'' contains a halogen such as bromine, have fire-retardant or extinguishing characteristics; compounds of this type, therefore, have dual application.

It will be understood that various changes may be made in the illustrative methods and compounds referred to hereinabove without departing from the scope of the present invention. It is intended, therefore, that the preceding description should be construed as illustrative only and not in a limiting sense.

We claim:

1. An acylamide of a β-cyano-ethenesulfonyl substituted aminoarene having the formula R' — SO$_2$ NH — Ar — SO$_2$ CH = CH — CN
   wherein R' is alkyl of from 1 to 16 carbon atoms; CH$_2$=CH—;

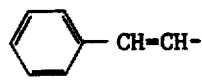 CH=CH— ;

phenyl or phenyl substituted by alkyl of 1 to 16 carbon atoms, halogen, nitro, hydroxy, alkoxy of 1 to 16 carbon atoms, carbalkoxy of 1 to 2 carbon atoms, or carboxamide; bipheny or naphthyl; and Ar is phenylene; phenylene substituted by nitro, chloro or methyl; biphenylene; or naphthylene.

2. The acylamide of claim 1, wherein Ar is

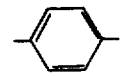

or

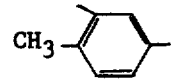

R' is selected from the group consisting of alkyl of 1 to 16 carbon atoms; phenyl; phenyl substituted by alkyl of 1 to 16 carbon atoms, halogen, hydroxy or methoxy; 2-naphthyl; and

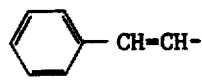 CH=CH—

3. The acylamide of claim 1, wherein Ar is

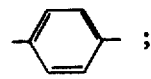 ;

and

R' is selected from the group consisting of alkyl of 1 to 16 carbon atoms; phenyl; phenyl substituted by methyl, halogen, hydroxy or methoxy; 2-naphthyl; and
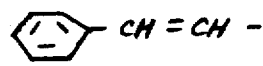
* * * * *

UNITED STATES PATENT OFFICE
CERTIFICATE OF CORRECTION

Patent No. 3,943,154　　　　　　　　　　Dated　March 9, 1976

Inventor(s) Sven U.K.A. Richter et al

It is certified that error appears in the above-identified patent and that said Letters Patent are hereby corrected as shown below:

Column 9, lines 47-48: "4-sulfinylimido-3fluorophenyl sulfone," should read -- 4-sulfinylimido-3-fluorophenyl sulfone, --.

Column 10, line 12: "On the the" should read -- On the other --; line 22: "carbodimide" should read -- carbodiimide --; line 60: "conventionally" should read -- conveniently --.

Column 12, line 45: "chlorofrom" should read -- chloroform --.

Column 16, lines 27-28: "3-(4-aminobenzenesulfonyl acrylonitrile" should read -- 3-(4-aminobenzenesulfonyl)acrylonitrile --.

Column 22, line 68 to column 23, line 1: "3-[4-(4-ACETAMIDOBENZENESULFONAMIDO)BENZENESULFONYL]acrylonitrile" should read --
3-[4-(4-Acetamidobenzenesulfonamido)benzenesulfonyl]acrylonitrile--; column 23, lines 56-57: "3-[4-(4-DICHLOROCARBOSTYRENESULFONAMIDO)BENZENESULFONYL]acrylonitrile" should read -- 3-[4-(4-dichlorocarbostyrenesulfonamide)benzenesulfonyl]acrylonitrile --.

Column 26, line 63: "onehalf" should read -- one-half --.

UNITED STATES PATENT OFFICE
CERTIFICATE OF CORRECTION

Patent No. 3,943,154                     Dated    March 9, 1976

Inventor(s) Sven U.K.A. Richter et al

It is certified that error appears in the above-identified patent and that said Letters Patent are hereby corrected as shown below:

Column 27, line 39:   "NaoH" should read -- NaOH --.

Columns 39-40, Table I cont'., column 2, Example 29.2, 1st formula:

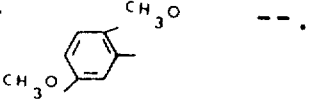   should read

Columns 39-40, Table I cont'., column 2, Example 38, 2nd formula from the bottom:

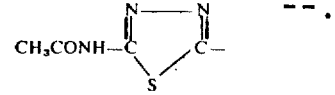   should read

Columns 39-40, Table II, column 8, line 1 under B. subtilis:  the blank space should be -- a dash (-) --.

Columns 41-42, Table II cont'., columns 1-4, the formula:
"                           "     should read

--

Column 43, line 68:   "bipheny" should read -- biphenyl --.

Signed and Sealed this

Seventeenth Day of August 1976

[SEAL]

Attest:

RUTH C. MASON
*Attesting Officer*

C. MARSHALL DANN
*Commissioner of Patents and Trademarks*